(12) United States Patent
Xie et al.

(10) Patent No.: US 9,645,130 B2
(45) Date of Patent: May 9, 2017

(54) MEASURING PROPERTIES OF A MULTIPHASE MIXTURE FLOW

(71) Applicant: SCHLUMBERGER TECHNOLOGY CORPORATION, Sugar Land, TX (US)

(72) Inventors: Cheng-Gang Xie, Sawston (GB); Mehdi Hizem, Paris (FR); Rolf Rustad, Radal (NO)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 501 days.

(21) Appl. No.: 13/968,145

(22) Filed: Aug. 15, 2013

(65) Prior Publication Data

US 2013/0327154 A1 Dec. 12, 2013

Related U.S. Application Data

(63) Continuation-in-part of application No. 12/769,781, filed on Apr. 29, 2010, now Pat. No. 8,536,883.

(51) Int. Cl.
*G01N 33/28* (2006.01)
*G01N 22/00* (2006.01)
(Continued)

(52) U.S. Cl.
CPC ............. *G01N 33/28* (2013.01); *G01N 22/00* (2013.01); *G01N 33/2823* (2013.01);
(Continued)

(58) Field of Classification Search
CPC ........ G01R 27/14; G01R 27/02; G01R 27/08; G01R 27/2605; G01L 1/205; G01N 33/28; G01N 33/2823; G01N 22/00
(Continued)

(56) References Cited

U.S. PATENT DOCUMENTS 2,456,117 A * 12/1948 Feller .................. G01N 27/06
324/445
3,849,721 A 11/1974 Calvert
(Continued)

FOREIGN PATENT DOCUMENTS

EP 1901094 A1 3/2008
EP 1983357 A1 10/2008
(Continued)

OTHER PUBLICATIONS

International Search Report and Written Opinion issued in PCT/IB2011/000514 on Dec. 26, 2011, 11 pages.
(Continued)

*Primary Examiner* — Jermele M Hollington
*Assistant Examiner* — Christopher McAndrew

(57) ABSTRACT

Properties of a multiphase mixture flow are measured in a blind-tee. The measured properties include the permittivity and/or the conductivity of the multiphase mixture flowing through a conduit. The permittivity and/or conductivity are measured at liquid-rich region(s) in a blind-tee section of the conduit and are used to determine properties of a liquid phase of the multiphase fluid flow, including one of the water conductivity, water in liquid ratio and water volume fraction. One or more electromagnetic sensors may be used in the blind-tee to measure the permittivity and/or conductivity. The sensors may be in contact with the multiphase flow or be disposed behind a dielectric window.

22 Claims, 14 Drawing Sheets

(51) Int. Cl.
*G01R 27/14* (2006.01)
*G01R 27/02* (2006.01)
*G01R 27/26* (2006.01)
*G01R 27/08* (2006.01)

(52) U.S. Cl.
CPC .............. *G01R 27/02* (2013.01); *G01R 27/08* (2013.01); *G01R 27/14* (2013.01); *G01R 27/2605* (2013.01)

(58) Field of Classification Search
USPC ................... 73/61.44; 324/637, 691; 702/45
See application file for complete search history.

(56) References Cited

U.S. PATENT DOCUMENTS

| | | | |
|---|---|---|---|
| 3,891,391 A | 6/1975 | Boone | |
| 3,944,910 A | 3/1976 | Rau | |
| 3,967,201 A * | 6/1976 | Rorden | E21B 47/122 340/850 |
| 4,396,063 A * | 8/1983 | Godbey | E21B 43/24 166/250.06 |
| 4,574,827 A * | 3/1986 | Konak | F16L 41/02 137/599.01 |
| 4,574,837 A * | 3/1986 | Aggour | F16L 41/00 137/561 A |
| 4,704,581 A | 11/1987 | Clark | |
| 5,051,922 A * | 9/1991 | Toral | G01F 1/74 700/285 |
| 5,127,272 A * | 7/1992 | Dean | G01F 1/74 73/200 |
| 5,182,909 A * | 2/1993 | Stellwagen | F15B 11/162 60/426 |
| 5,199,639 A * | 4/1993 | Kobayashi | B05B 1/1645 239/11 |
| 5,243,290 A | 9/1993 | Safinya et al. | |
| 5,345,179 A | 9/1994 | Habashy et al. | |
| 5,390,547 A * | 2/1995 | Liu | G01F 15/08 73/200 |
| 5,453,693 A | 9/1995 | Sinclair et al. | |
| 5,485,743 A | 1/1996 | Taherian et al. | |
| 5,570,744 A * | 11/1996 | Weingarten | B01D 17/00 166/357 |
| 5,589,642 A * | 12/1996 | Agar | G01F 1/74 73/861.04 |
| 5,597,961 A * | 1/1997 | Marrelli | G01F 1/363 73/61.44 |
| 5,793,216 A | 8/1998 | Constant | |
| 5,821,405 A * | 10/1998 | Dickey | G01D 11/24 73/170.29 |
| 6,083,405 A * | 7/2000 | Tanaka | C02F 1/28 210/170.05 |
| 6,089,039 A * | 7/2000 | Yamauchi | F25B 6/04 165/113 |
| 6,097,786 A | 8/2000 | Groves et al. | |
| 6,128,962 A * | 10/2000 | Marrelli | G01F 1/74 324/638 |
| 6,234,030 B1 * | 5/2001 | Butler | E21B 21/01 73/195 |
| 6,269,320 B1 * | 7/2001 | Otto | B64D 15/20 244/134 C |
| 6,532,826 B1 * | 3/2003 | Dou | G01F 1/74 73/861.04 |
| 6,658,944 B2 | 12/2003 | Melnikov et al. | |
| 6,776,054 B1 * | 8/2004 | Stephenson | G01F 1/44 73/861.63 |
| 6,831,470 B2 | 12/2004 | Xie et al. | |
| 6,938,506 B2 * | 9/2005 | Henry | G01D 11/24 73/866.5 |
| 6,940,286 B2 | 9/2005 | Wang et al. | |
| 7,363,160 B2 | 4/2008 | Seleznev et al. | |
| 7,376,514 B2 | 5/2008 | Habashy et al. | |
| 7,469,188 B2 | 12/2008 | Wee | |
| 7,481,118 B2 | 1/2009 | Nyfors | |
| 7,503,227 B2 | 3/2009 | Davis et al. | |
| 7,624,652 B2 | 12/2009 | Wee et al. | |
| 7,908,930 B2 | 3/2011 | Xie et al. | |
| 7,942,065 B2 | 5/2011 | Xie | |
| 8,224,588 B2 * | 7/2012 | Wee | G01F 1/66 702/30 |
| 2005/0140368 A1 * | 6/2005 | Freedman | E21B 49/08 324/303 |
| 2007/0024505 A1 * | 2/2007 | Geisheimer | H01Q 1/002 343/700 MS |
| 2008/0148867 A1 * | 6/2008 | Nyfors | G01F 1/40 73/861.63 |
| 2008/0224705 A1 | 9/2008 | Simon et al. | |
| 2008/0264788 A1 * | 10/2008 | Uthemann | G01N 27/283 204/412 |
| 2008/0284451 A1 * | 11/2008 | Binder | G01R 27/04 324/606 |
| 2009/0126502 A1 * | 5/2009 | Wee | G01F 1/44 73/861.04 |
| 2010/0117685 A1 * | 5/2010 | Kong | G06F 13/4072 327/74 |

FOREIGN PATENT DOCUMENTS

| | | |
|---|---|---|
| EP | 2015109 A1 | 1/2009 |
| GB | 2430493 A | 3/2007 |
| GB | 2451994 A | 2/2009 |
| GB | 2451994 B | 5/2011 |
| WO | 2007129897 A1 | 11/2007 |
| WO | 2009010132 A2 | 1/2009 |

OTHER PUBLICATIONS

Carter, et al, "Phasing Out Separation", Middle East and Asia Reservoir Review, No. 3 (2002) pp. 26-31.

* cited by examiner

MEASURING PROPERTIES OF A MULTIPHASE MIXTURE FLOW

CROSS-REFERENCE TO RELATED APPLICATION

This application is a continuation-in-part of co-pending U.S. patent application Ser. No. 12/769,781 filed Apr. 29, 2010, which is incorporated herein by reference in its entirety.

BACKGROUND

Embodiments of the present invention relate to determining properties of a flow of a multiphase mixture comprising a mixture of a gas phase, an oil phase and a water phase.

It is desirable during the production of oil and gas to carry out flow measurements to determine the flow rates of individual phases of the multiphase flow. In particular, measurement of the volume fractions and flow velocities of e.g., oil, gas and water in a conduit, such as a pipe, is highly desirable. It is also desirable to determine properties of the multiphase mixture, such as salinity of water in the mixture, as this provides information about the mixture and may affect other measurements being made on the multiphase mixture.

However, in general it may be difficult to obtain measurements or determine properties of the flow of the different phases when they flow simultaneously through a pipe.

This difficulty is primarily due to the wide variety of flow regimes such a multiphase flow can take. For example, the three phases can be well mixed together with one as the continuous phase and the other two dispersed within it. Mostly there is phase separation between gas and liquid with the liquid often moving at a much lower velocity than the gas.

When gas is the dominant phase, a commonly encountered flow regime in a vertical pipe is for the gas to travel along the centre of the pipe with dispersed droplets of oil and water within it, whilst the majority of the oil and water travels along the pipe wall which itself may comprise entrained gas bubbles. In a near horizontal pipe, the majority of the oil and water tends to travel along the bottom part of the pipe, with gas traveling along the pipe top part.

Additionally, flow phase and velocity distributions may alter both spatially and temporally. Sudden or gradual variation in flow rates of one phase or another may cause a change in flow regime. Also, due to the high pressure encountered deep underground or below seabed, a flow which is mixed or in bubble-flow regime can become dominated by a discernible high gas fraction as the pressure drops nearer the ground or subsea surface and the gas expands and/or comes out of solution.

Multiphase flowmeters and sensors for determining properties of multiphase flows are available and have been suggested in the prior art. In general, multiphase flowmeters and multiphase sensors are positioned such that the meters/sensors encounter an identified set of flow regimes. For example, meters/sensors are often positioned in vertical sections of a pipe transporting the multiphase mixture with the use of a horizontal blind-tee inlet pipe section; as annular flow is the dominant flow regime in such a vertical pipe section when gas is the dominant phase, the readings from the sensors can be analysed to determine properties of the multiphase mixture based upon the understanding that the flow regime is annular.

The use of electromagnetic methods, such as microwaves, has been suggested because of their high measurement sensitivity to the presence of the water phase in a multiphase flow (water permittivity/conductivity is much higher than the permittivity/conductivity of the hydrocarbon oil-gas phases). U.S. Pat. No. 6,831,470 of the Applicant teaches the use of a microwave open-ended coaxial reflection probe to measure the reflected-signal amplitude-attenuation and phase-shift values representative of mixture permittivity and mixture conductivity to obtain an online estimate of water conductivity of a multiphase flow. An estimate of the water-to-liquid ratio (WLR) immune to water-salinity change is also possible if the liquid layer in the vicinity of the probe is intermittently (in time) substantially free of entrained gas and has a thickness higher than the probe's depth of investigation.

U.S. Pat. No. 7,942,065, of the Applicant utilises a transmission electromagnetic approach, in combination with a venturi differential-pressure sensor (for total flow rate) and a gamma-ray radiation sensor (for gas-liquid mixture density). The across-pipe transmission microwaves are used to measure the amplitude-attenuation and phase-shift values representative of mixture permittivity and mixture conductivity over the vertical pipe cross-section of the venturi throat, for water and hydrocarbon (oil/gas) discrimination. The gamma rays are employed in the same venturi-throat pipe cross-section for gas and liquid (oil/water) discrimination, by measuring the average fluid mixture density across pipe. By employing three-phase density and permittivity and/or conductivity mixing rules, measures of water fraction, oil fraction (hence of the WLR) and gas fraction can be obtained. Measured venturi differential pressure and/or further microwave sensors measured flow velocity in the venturi can be used to provide an estimate of the individual phase flow rate, from the measured individual phase fraction and the total flow rate and/or the phase velocity data. As disclosed in U.S. Pat. No. 6,831,470, RF/microwave transmission approach also permits online water-conductivity estimate from the measured values representative of the mixture permittivity and mixture conductivity.

U.S. Pat. No. 5,485,743 of the Applicant discloses a method for measuring multiphase flows in a pipe using an array (e.g., twelve) of microwave antennas arranged around the pipe. Each antenna is capable of transmitting microwave energy (at one or more frequencies) into the pipe and detecting propagated microwave energy in the pipe. Microwave energy from each antenna is transmitted in turn while the propagated microwave energy is detected at the non-transmitting antennas so as to generate multiple amplitude-attenuation and phase-shift output signals. The output signals from all antennas combinations are interpreted by an appropriate mathematical inversion algorithm, e.g., as flow permittivity-conductivity cross-sectional tomographic images, so as to measure the flow phase fractions and to visualise flow phase distributions in the pipe. Only absolute measurements are disclosed and no differential-measurement scheme (of measuring amplitude-attenuation ratio and phase-shift difference of chosen two receivers, with respect to one chosen transmitter) is mentioned.

U.S. Pat. No. 7,624,652 discloses a differential-measurement configuration based on one transmitter and two receivers, where the amplitude-attenuation ratio and/or phase-shift difference of the two receivers, measured at multiple frequencies with respect to a chosen transmitter, are used for flow-mixture dielectric-constant determination.

In all of these electromagnetic methods, a measure of the permittivity and conductivity of the flow mixture is involved by analysing phase-shift and amplitude-attenuation. Permittivity and/or conductivity data allows a host of useful flow information within the conduit to be obtained, such as water conductivity, water fraction, WLR, flow rates of individual phases, in combination with a differential pressure and a nuclear mixture-density measurement; information as to the distribution of fluid phases within the conduit can be obtained from measurements of a plurality of RF/microwave antennas arranged around the conduit.

SUMMARY

In embodiments of the present invention, a sensor(s) is positioned in a blind-tee and used to determine liquid properties (water conductivity, water volume fraction, water-in-liquid ratio and/or the like) of a multiphase mixture flowing through the blind-tee. Connected to a horizontal oil-gas production transportation pipe, the blind-tee comprises a horizontal section of pipe that is in fluid communication with a vertical section of the pipe and is configured to provide that the multiphase mixture flows into the horizontal section of pipe and out through the vertical section of pipe. The vertical section may extend vertically upwards from the horizontal section or vertically downwards from the horizontal section. In some embodiments, the sensor is coupled with the horizontal section of the blind-tee. In other embodiments, the sensor is coupled with an end of the blind-tee. In some embodiments, multiple sensors are disposed at different locations in the blind tee.

In embodiments of the present disclosure, the sensor may comprise one or more antennas/transceivers for transmitting an input electromagnetic signal at one or a plurality of frequencies into the multiphase mixture and receiving a received electromagnetic signal that has passed through at least a portion of the multiphase mixture. In some aspects, properties such as amplitude-attenuation and/or phase-shift of the received electromagnetic signal relative to the input, at one or a plurality of frequencies, may be used to determine permittivity and/or conductivity properties of the multiphase mixture. In some embodiments, the sensor(s) may be disposed at locations in the blind-tee that are liquid rich because of the flow of the multiphase mixture through the blind-tee.

Previously, the estimate of the permittivity and/or conductivity involves taking into account factors influencing the quality of the transmitted and/or received signal, such as the thermal stability of the electronics-circuit amplification-gain applied to the receiving and/or transmitting antennas, the variations in the antennas' connecting cables and/or in the antennas' load impedances due to e.g., changes in fluid temperature or aging, etc.

This is normally not a problem in a controlled laboratory environment, since such factors are usually known and can be accounted for by appropriate calibrations and/or corrections. However, in a permanent or unmanned oilfield measurement environment such as offshore and/or subsea, gain levels in the electronics measurement circuits can drift over time and/or with temperature. Additionally, the transmitted and/or received signal may be affected by other factors, such as a build-up of wax material in front of the antenna, aging of the circuitry, etc. These latter problems can be particularly problematic when the flow measurement is taken in an oilfield environment, where very high pressures and temperatures exacerbate these factors.

In some embodiments of the disclosure, the permittivity and/or conductivity of a multiphase fluid flowing through a blind-tee is measured. The permittivity and/or conductivity may be determined by measuring the signal from a first electromagnetic transmitter to a first electromagnetic receiver separated by a first distance, measuring the signal from the first electromagnetic transmitter to a second electromagnetic receiver separated by a second distance, measuring the signal from a second electromagnetic transmitter to the first electromagnetic receiver separated by a distance substantially equal to the second distance, measuring the signal from the second electromagnetic transmitter to the second electromagnetic receiver separated by a distance substantially equal to the first distance, and wherein the first and second distances are substantially different, followed by combining the four signals to obtain a measurement of the phase-shift and amplitude-attenuation substantially independent of the gain values applied to the paths of receivers and transmitters to provide an estimate of the mixture permittivity and/or conductivity of the multiphase fluid.

Thus, by combining the four signals in a particular manner it has been found to be possible to obtain a measure of phase-shift and amplitude-attenuation which is substantially independent of factors other than those provided by the multiphase fluid travelling through the conduit. Therefore, a more accurate estimate of permittivity and/or conductivity can be obtained and the accuracy is maintained over time, despite drifts which may occur in the gain values of the measurement paths related to both the transmitting and the receiving antennas.

The values of permittivity and/or conductivity obtained are also called complex permittivity. The "true" permittivity characterizing energy storage and the conductivity due to energy-dissipation losses can be combined in a known manner, given the measurement frequency.

Typically, the transmitting and receiving antennas are able to operate as a pure magnetic dipole and/or as a pure electric dipole. In some aspects, the antennas are capable of operating as both pure magnetic and pure electric dipoles. In embodiments of pure magnetic-dipole antennas covered by a protective dielectric-material window, mixture permittivity and in particular mixture conductivity can still be effectively determined from magnetic-dipole induced amplitude-attenuation and/or phase-shift properties of the received electromagnetic signal. The antennas with the dielectric window may be substantially flush mounted with the blind-tee and build-up of deposits on the window of the antennas may not adversely affect the determination of the permittivity and/or conductivity of multiphase flow mixture containing water. Therefore the subsequent determination of the liquid properties (including the water conductivity) may not be adversely affected.

For example, a simple antenna would be an open-ended coaxial probe that behaves as an electric dipole; the determination of mixture (hence water) conductivity may be affected by wax deposition on its open-ended sensing aperture. A more elaborate and robust design of antenna is shown in EP 1901 094 of the Applicant which is a cross-dipole of pure magnetic-dipole antennas. The orthogonality of the two cross dipole modes is ensured with a high degree of isolation. Only one magnetic dipole of the two cross dipoles may be used in an antenna design in some embodiments. Antenna as a superposition of a substantially pure electric dipole and a substantially pure magnetic dipole is shown in EP 1983 357 of the Applicant.

In some embodiments, the signals may be transmitted and received at one or more frequencies in the radio frequency (RF) and/or microwave frequency spectrum. For example, the signals may have a frequency or multiple frequencies of from 10 MHz to 10 GHz.

In some embodiments, at least two transmitters and at least two receivers may be used for each measurement frequency. In such embodiments, the four available signals may be combined to eliminate undesirable influencing factors. In such embodiments, the distance between a first transmitter and a first receiver (the first distance) and that between the first transmitter and a second receiver (the second distance) may be significantly different to each other. This means that the difference of the first and the second distance may be at least 10%, or at least 20%.

In some embodiments, the distance between a second transmitter and the first receiver is substantially equal to the second distance. Also the distance between a second transmitter to the second receiver is substantially equal to the first distance. As used herein, the term "substantially equal" means that the distances are within the order of 1% of the first and second distance respectively and more preferably within 0.5%.

Typically the conduit sections of the blind-tee have a circular cross-section (but embodiments of the present invention are not limited to blind-tees comprising pipe sections having a circular cross-section). The transmitters and receivers are typically flush-mounted on the inside face of the conduit. In some aspects, the transmitters and receivers may be located at the same axial plane of the conduit or they may be positioned at differing axial planes.

In some embodiments, a multiphase flow sensor is provided comprising at least two electromagnetic transmitters and at least two electromagnetic receivers, coupled with electromagnetic generation and reception circuitry respectively, and coupled to a microprocessor, wherein the transmitters, receivers, circuitry and the microprocessor are arranged to carry out the method described herein.

In an embodiment where the conduit of the blind-tee has a circular cross-section and the transmitters and receivers are all arranged in the same axial position, the spacing requirements of the invention requires that they be arranged substantially with a line of symmetry passing through the centre of the conduit. This means that the second transmitter and second receiver must be positioned in effective mirror image positions relative to the first transmitter and first receiver respectively about the centre line of symmetry. This ensures that the relative positioning and spacing requirements of the invention are met.

In some embodiments, more than two transmitters and/or more than two receivers may be used. Additional transmitters and receivers can give further improvements in accuracy and/or in versatility by covering different regions or depths of a pipe cross section and/or of different pipe cross sections, however only the basic combinations of two of each at a time are necessary in order to eliminate the undesirable factors affecting the signals. Therefore, there is a tomography flow imaging capability from having additional transmitters and receivers in the same cross-sectional plane and/or in different cross-sectional planes. However, a modest number of antennas acting as transmitters or receivers or both, say up to sixteen in a cross-sectional plane, can be advantageously chosen as a full tomography system. Additionally, for a non-tomography system, from two to six transmitters provides a good balance between measurement speed, pipe-area coverage, accuracy and cost.

In some embodiments, an arrangement with more than two transmitters or more than two receivers may be used to generate more than one set of four "absolute measurements". For example, an arrangement with two transmitters and four receivers can generate eight absolute measurements. From these eight measurements it is possible to generate two separate groups (each group being related to each transmitter) of four absolute readings. Thus, two compensated (transmitter-receiver path gain-immune) measurements according to the invention can be generated by differencing the same group and averaging the group-differences appropriately to provide greater accuracy.

Another advantage of having more than two transmitters or more than two receivers is that they can be arranged around the conduit to probe different regions or depths of the conduit.

For example two transmitters could be positioned, say 30° apart. Two receivers could then be positioned each a further 30° from the transmitters. Two additional receivers could then be positioned opposite the respective transmitters. By use of the "near" receivers, information on the condition in the vicinity of the inner wall of the conduit can be obtained. By use of the "far" receivers, information on the cross-pipe diameter can be obtained. Such measurements made rapidly may be combined to derive further information on the instantaneous spatial distribution of the phases of the flow. Thus, the first distance may span substantially across the conduit and the second distance may span substantially adjacent an inside wall of the conduit.

In embodiments of the present invention, the water conductivity (hence salinity) can be determined from the mixture permittivity and/or conductivity, as described in U.S. Pat. No. 6,831,470, which is incorporated herein by reference for all purposes. The derived salinity may be used to determine origins of the water in the multiphase flow or wet-gas flow mixture, i.e., condensed (fresh) water, formation water, injected water and/or the like and may be further used so that measurement of water fraction, water-in-liquid ratio (WLR) and/or the like from other sensors (such as a dual-energy gamma-ray system) are made correctly by taking into account any changes in salinity. Furthermore, the water fraction and/or WLR of the multiphase or wet-gas flow mixture can be derived from the mixture permittivity and/or conductivity of the flow by the use of appropriate permittivity and conductivity mixing rules. The detection of first water, changes in water volume fraction and in the water conductivity (salinity) in a subsea gas well is particularly important for flow assurance purposes. The risks of hydrate plugging and/or corrosion to long subsea flow lines may be mitigated by injecting a correct dosage of hydrate and/or corrosion inhibitors with the appropriate sensor input.

BRIEF DESCRIPTION OF THE DRAWINGS

The present disclosure is described in conjunction with the appended figures.

Figure 1:
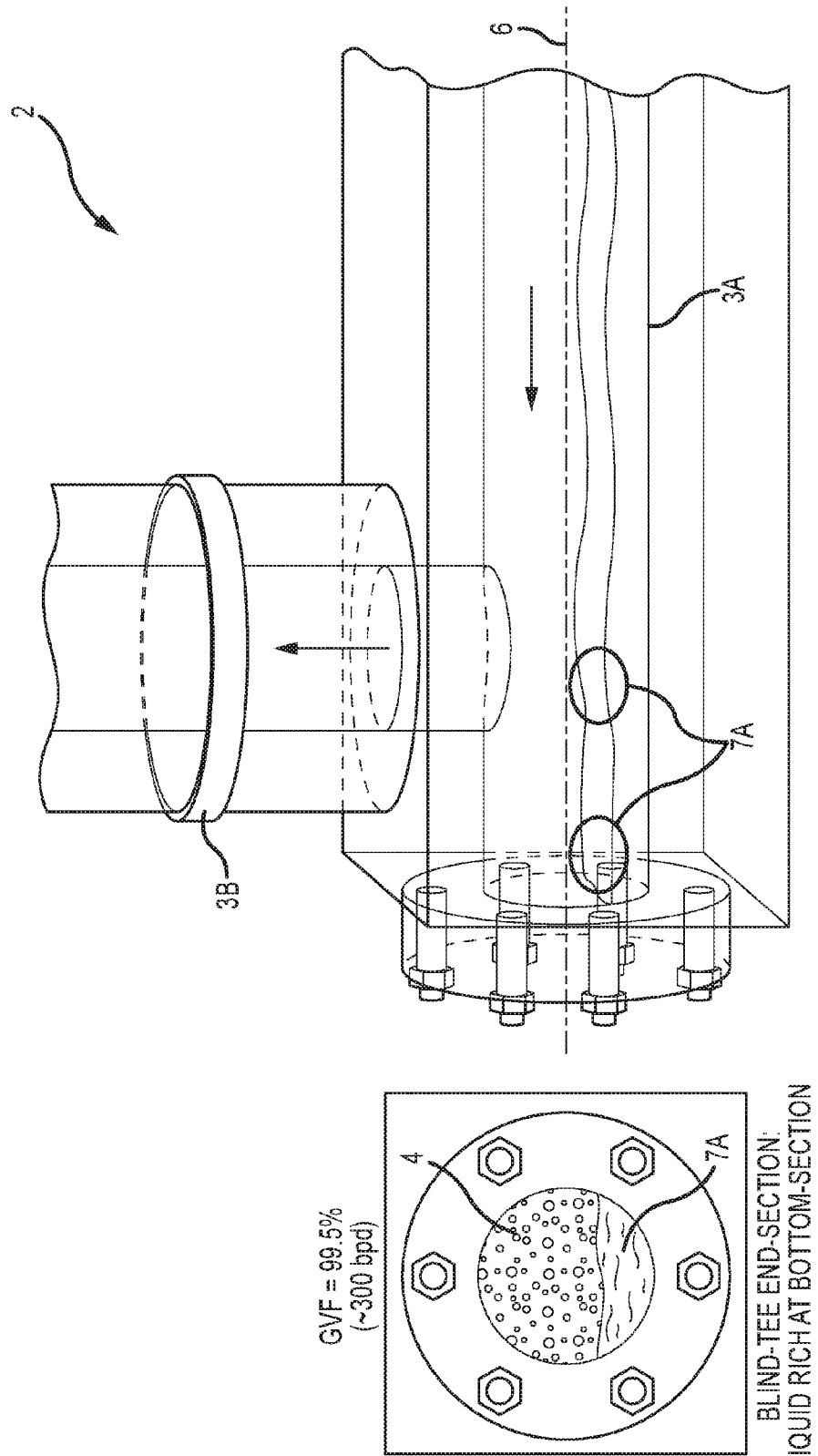
FIG. 1 illustrates high gas-volume-fraction turbulent flow of a multiphase mixture through a blind-tee, with liquid (water) regions indicated.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class or any combination of instructions, data structures, or program statements. A code segment may be coupled to another code segment or a hardware circuit by passing and/or receiving information, data, arguments, parameters or memory contents. Information, arguments, parameters, data, etc., may be passed, forwarded, or transmitted via any suitable means including memory sharing, message passing, token passing, network transmission, etc.

Merely by way of example, early water detection and water-salinity change detection may be used for subsea wet-gas well flow assurance applications in terms of mitigating the risks of hydrate formation and corrosion in subsea long flow lines. The use of electromagnetic methods, such as microwaves, has previously been used because of their high measurement sensitivity to the presence of the water phase in a multiphase flow (water permittivity/conductivity is much higher than the permittivity/conductivity of the hydrocarbon oil-gas phases). U.S. Pat. No. 6,831,470 of the Applicant teaches the use of a microwave open-ended coaxial reflection probe to measure values representative of the mixture permittivity and mixture conductivity to obtain an online estimate of water conductivity (salinity) of a multiphase flow. An estimate of the water-to-liquid ratio (WLR) corrected for to water-salinity change is also possible if the liquid layer in the vicinity of the probe is substantially free of entrained gas and has a thickness higher than the probe's depth of investigation.

Whereas previously sensors have often been used in vertical sections of a pipeline, in embodiments of the present disclosure, a high sensitivity for early water detection and water-salinity change detection is achieved by using an electromagnetic sensor that is disposed in a horizontal blind-tee section that is often used as an inlet configuration of a vertically installed multiphase flow meter. In this location, it has been found through experimental studies that although the flow regime is turbulent under very high gas-flow conditions, if the sensor is positioned in the lower part of the horizontal section of the blind-tee or a lower portion of the an end section of the blind-tee, i.e., below the midpoint of the pipe section making up the horizontal section of the blind tee, the sensor is in a location that is locally liquid (water) rich.

FIG. 1 illustrates high-gas turbulent flow of a multiphase mixture through a blind-tee. The turbulent flow was captured in flow visualization studies in combination with microwave sensor cross-pipe and near-wall measurements.

As shown in FIG. 1, a fluid is flowed through a bind-tee 2. The blind-tee 2 comprises a horizontal conduit section 3A, a vertical conduit section 3B and an end section 4. The horizontal conduit section 3A has a mid-point 6 describing a plane that bisects the horizontal conduit section 3A. As can be seen in FIG. 1, the flow of the fluid is turbulent as the fluid interacts with the end section 4 and its flows is changed by 90 degrees as the flow passes from the horizontal conduit section 3A to the vertical conduit section 3B.

However, as found by Applicants and illustrated in FIG. 1, a liquid rich region(s) 7A is generated in the turbulent flow at the bottom of the horizontal conduit section 3A. Moreover, the liquid rich region(s) 7A is more pronounced than the liquid layer seen in the flow upstream and/or downstream of the liquid rich region(s) 7A.

In one embodiment of the present invention (not shown), the blind-tee 2, may be rotated 180 degrees such that the vertical section 3B extends vertically downwards from the horizontal conduit section 3A. In such a configuration, Applicants have found pronounced liquid rich regions on the bottom half of the horizontal conduit section 3A between the opening of the vertical conduit section 3B and the end section 4 and on the bottom half of the horizontal conduit section 3A appurtenant to and upstream of the opening of the vertical conduit section 3B.

Applicants have found that while a blind-tee does not separate the phases of the multiphase mixture, it produces locations at the bottom of the horizontal section that are in general liquid rich. It has been found that these locations may be more liquid rich than other pipe locations whatever the composition/gas-volume-fraction/liquid-fraction of the multiphase mixture.

Figure 2A:
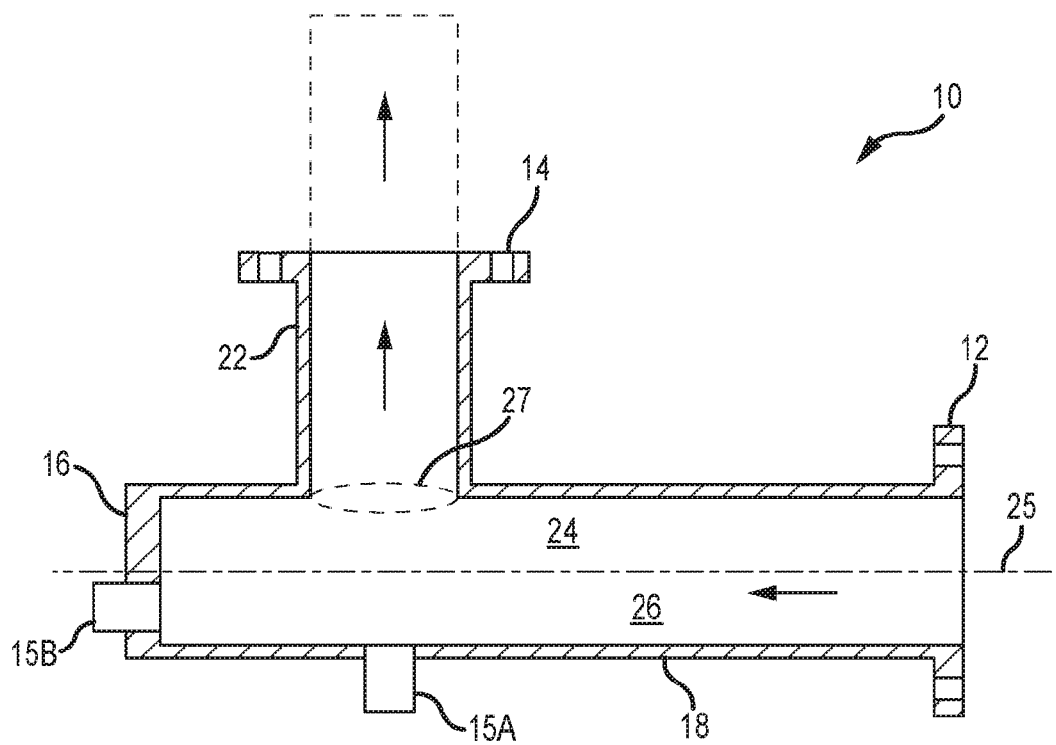
FIGS. 2A & B illustrate sensor systems for determining liquid properties (water conductivity/salinity, water volume fraction and/or water liquid ratio) of a multiphase mixture flowing through a blind-tee conduit, in accordance with an embodiment of the present invention.

FIG. 2A illustrates a system for determining liquid properties (water conductivity/salinity, water volume fraction and/or water liquid ratio WLR) of a multiphase mixture flowing through a conduit, in accordance with an embodiment of the present invention. The liquid properties measuring system comprises a blind tee 10 and one or more electromagnetic sensors 15.

The blind tee 10 comprises an inlet 12, a first conduit, 18, an outlet 14, an end section 16 and a second conduit 22. In use, the multiphase mixture flows into the blind tee 10 through the inlet 12, along the first conduit 18, through the second conduit 22 and out through the outlet 14. The end section 16 acts as a barrier that forces the flow of the multiphase mixture into the second conduit 22. In general, the blind tee 10 is configured so that the first conduit 18 is approximately horizontal and the second conduit 22 is approximately vertical. In embodiments of the present disclosure, the horizontal orientation of the first conduit provides that a bottom section 26 of the first conduit 18 is liquid rich and an upper section 24 of the first conduit 18 is gas rich. In some aspects of the present invention, the second conduit 22 may not be vertically upwards, but may be arranged vertically downwards, or at various angles with respect to the first conduit 18.

As described with respect to FIG. 1, it has been found that even in multiphase flows with high gas-to-liquid ratios (i.e., wet gas with gas volume fraction GVF>95%), liquid rich regions are produced in the bottom section 26. In some aspects, it has been found that liquid rich regions are produced in the blind tee 10 proximal to the end section 16 and/or beneath an opening 27 of the second conduit 22. In embodiments of the present invention, the first conduit may be of the order of 5 meters or less in length. In some embodiments, the first conduit may be of the order of meters in length. In some embodiments the first conduit may be of the order of less than a meter in length. In some aspects, it has been found that more pronounced liquid rich regions may be produced when the end section 16 and the opening 27 are separated by a section of the first conduit 18, as illustrated in FIG. 2.

In embodiments of the present invention, one or more electromagnetic sensors 15 (as further described herein) may be disposed below a central axis 25 of the first conduit 18. For example, the electromagnetic sensor 15A may be disposed in the bottom section 26 directly below the opening 27. Alternatively or in combination with the previous arrangement, the electromagnetic sensor 15B may be coupled with the end section 16. In embodiments of the present invention one or more of the electromagnetic sensors 15 may be disposed on the underside of the first conduit 18, in the bottom section 26 and/or coupled with the end section 16 below the central axis 25. Positioning of the electromagnetic sensor(s) 15 in the manner described herein in the blind tee 10 provides for interrogation of the liquid phase of the multiphase mixture and hence for determination of the properties (water conductivity/salinity, water volume fraction and/or WLR) of the liquid phase. To measure the properties of gas (e.g., permittivity change with pressure and/or temperature), one or more of the electromagnetic sensors 15 may be disposed on the topside of the first conduit 18, in the upper section 24 above the central axis 25, near the inlet section 12.

Figure 2B:
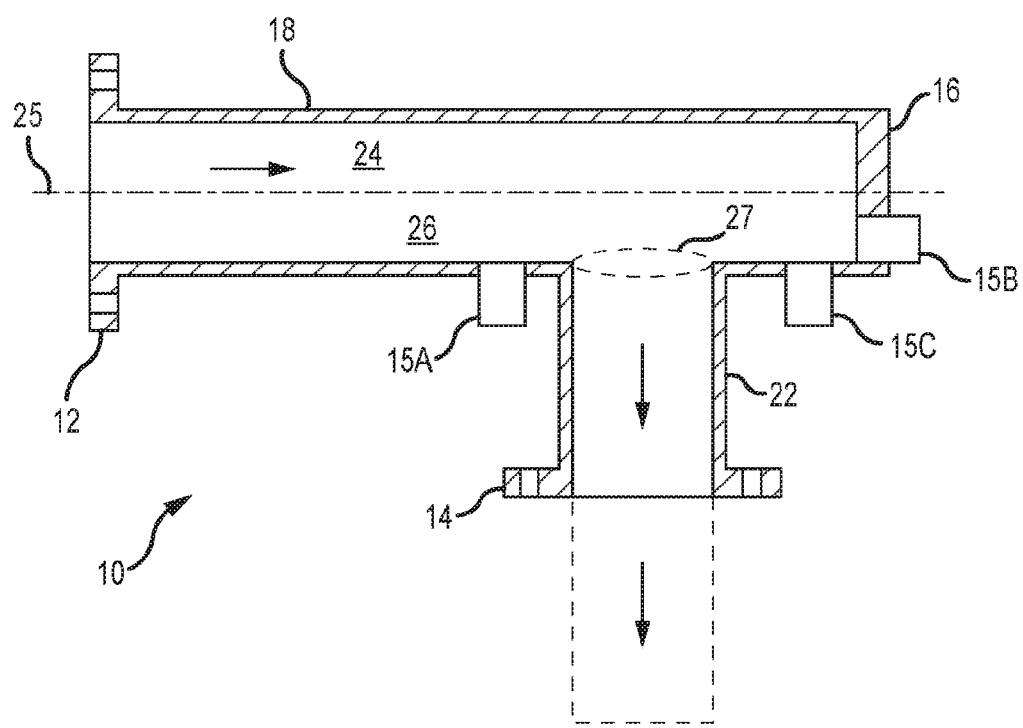

FIG. 2B illustrates a system for determining liquid properties (water conductivity/salinity, water volume fraction and/or water liquid ratio WLR) of a multiphase mixture flowing through a conduit, in accordance with an embodiment of the present invention. The blind-tee 10 is rotated through 180 degrees compared to FIG. 2A such that the vertical section 22 extends downwards with respect to the horizontal section 18.

Applicants have found that flow of a multiphase mixture through a blind-tee configured as in FIG. 2B produces liquid rich regions between the opening 27 and the end section 16 and/or proximal to and upstream of the opening 27. As such, in some embodiments of the present invention, the electromagnetic sensors 15A-C may be disposed at these liquid rich locations.

Figure 3A:
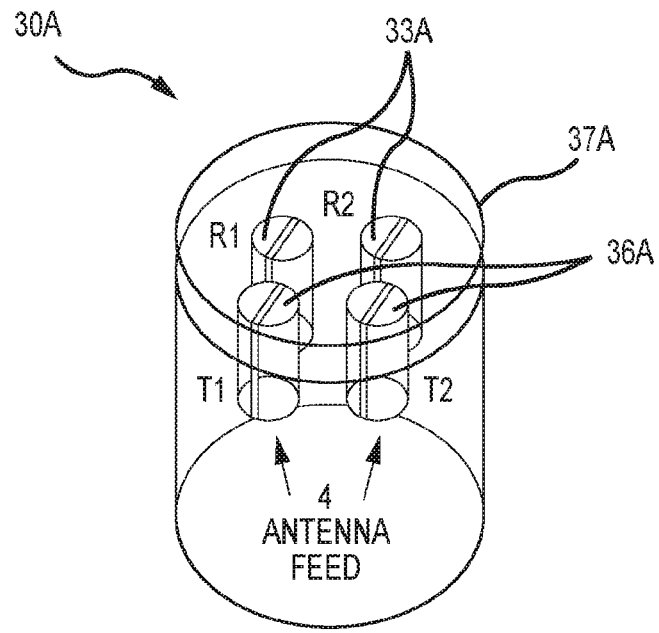
FIGS. 3A and 3B illustrate compact near-wall sensor antenna plugs that may be used to determine liquid properties of a multiphase mixture in accordance with one embodiment of the present invention.
Figure 3B:
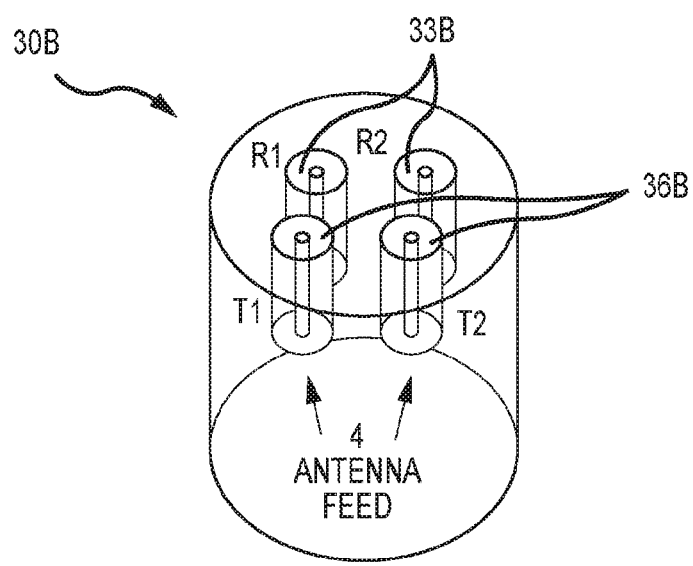

FIGS. 3A and 3B illustrate antenna plugs that may be used to determine liquid properties of a multiphase mixture in accordance with one embodiment of the present invention. As illustrated in FIG. 2, electromagnetic sensors, electromagnetic antennas, electromagnetic transceivers and/or the like may be disposed in the blind tee to interrogate the liquid properties of the multiphase mixture. As further described herein, the electromagnetic sensors, electromagnetic antennas, electromagnetic transceivers and/or the like may comprise many different forms, for example open-coaxial probe antennas and/or the like.

In some embodiments, the electromagnetic sensors, electromagnetic antennas, electromagnetic transceivers and/or the like may comprise an antenna plug 30 comprising a plurality of receivers 33 and a plurality of transmitters 36.

In FIG. 3A the receivers 33A and the transmitters 36A comprise 4 magnetic dipole antennas. In some embodiments, the sensor-aperture may be covered by a protective dielectric disc window 37A. The magnetic-dipole conductors (cross-aperture current probes) are configured in use not to contact the liquid phase of the multiphase mixture.

In FIG. 3B the receivers 33B and the transmitters 36B comprise 4 open-coaxial-probe antennas. In such embodiments, the receivers 33B and the transmitters 36B comprise coaxial centre conductors that are configured in use to contact the liquid phase of the multiphase mixture.

In some embodiments, a plurality of electromagnetic sensors placed at the bottom section and/or the end section of the blind-tee may be used to provide early water detection and water-conductivity (salinity) detection from rapid, of the order of 1 kHz or greater, measurements representative of multiphase flow mixture permittivity and/or conductivity.

Figure 4:
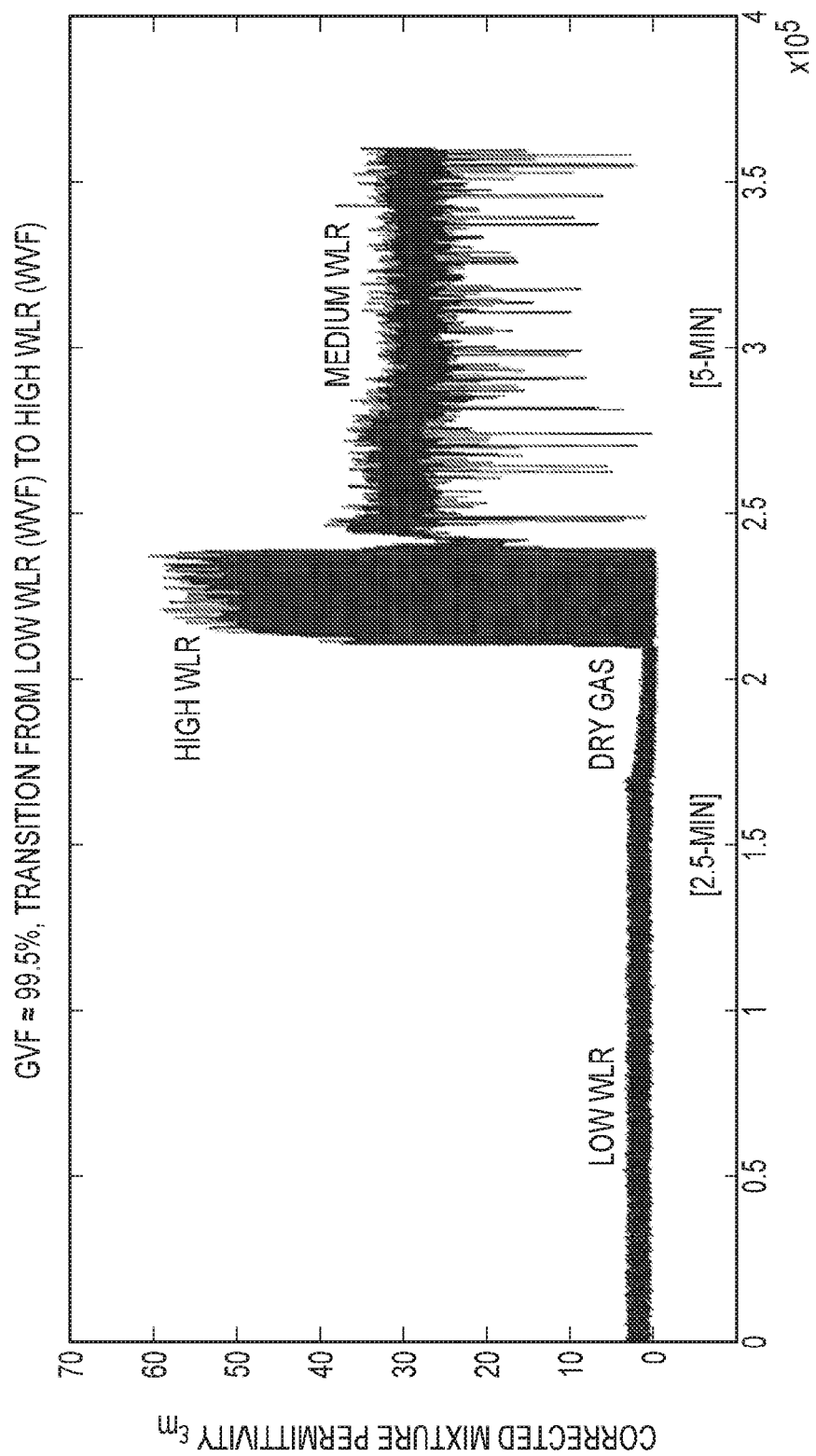
FIG. 4 illustrates correlation between permittivity of a liquid-rich phase of a multiphase mixture, as measured rapidly by a system in accordance with an embodiment of the present invention, and liquid properties of the multiphase mixture.

FIG. 4 illustrates correlation between permittivity of a liquid-rich phase of a multiphase mixture, as measured by a system in accordance with an embodiment of the present invention, and liquid properties of the multiphase mixture.

FIG. 4 illustrates rapid (about 1 kHz or greater) detection of changes in flow mixture permittivity by a microwave open-coaxial probe installed at end-section of the blind-tee. The data is from a flow-loop test for wet-gas of gas-volume-fraction GVF=99.5% and varying WLRs. FIG. 4 illustrates how permittivity of the liquid-rich multiphase mixture, as measured by the open coaxial probe, changes with water-to-liquid ratio of the multiphase mixture.

Figure 5:
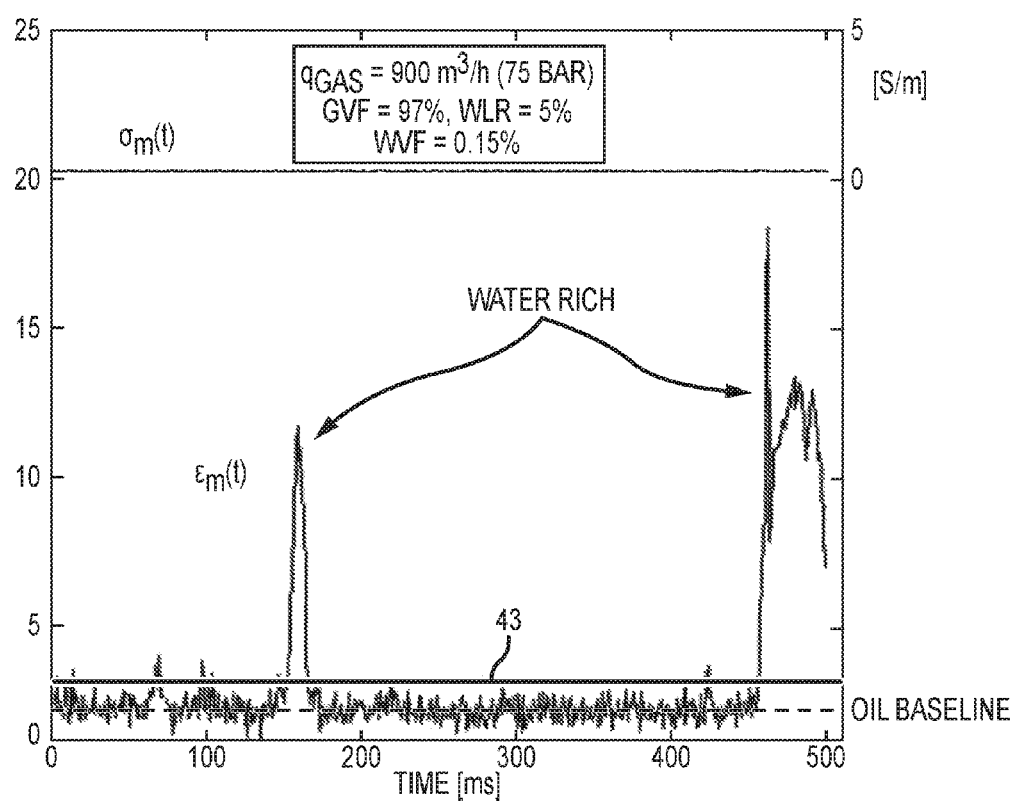
FIG. 5 illustrates rapid detection of changes in flow mixture permittivity and fresh-water conductivity by a microwave open-coaxial probe installed at end-section of the blind-tee, in accordance with an embodiment of the present invention.

FIG. 5 illustrates detection of changes in flow mixture permittivity and mixture conductivity by a microwave open-coaxial probe installed at end-section of the blind-tee, in accordance with an embodiment of the present invention. The data is from a flow-loop test for wet-gas flow (of fresh water) of GVF=97%, WLR=5%, water volume fraction WVF=0.15%. Threshold for detecting water-rich mixture permittivity data is illustrated as a yellow line 43.

As illustrated in FIG. 5, a rapid determination of the occurrence and frequency of mixture permittivity (and/or conductivity) above a chosen threshold (e.g., above the noise-floor of the oil-baseline reading) permits early water detection and trending of the water-volume-fraction (WVF=WLR (1−GVF)).

In embodiments of the present invention, the water-rich part of the mixture permittivity and/or the mixture conductivity instantaneous data (as shown in FIG. 5) may be chosen for the water-conductivity determination, by using the method similar to that disclosed in U.S. Pat. No. 6,831,470, incorporated herein by reference for all purposes.

For permanent subsea sensing applications of embodiments of the present invention, achieving a robust water-conductivity determination may require an RF/microwave measurement system that is immune to the short- and long-term drifts such as in the RF/microwave electronics gains, in the aging of connecting RF cables and in the sensing antennas installed at the blind-tee section. As such, an improved method of measuring phase-shift and amplitude-attenuation (for the determination of mixture permittivity and conductivity) that is immune to these influencing factors would be highly desirable.

Thus, the in some embodiments an integrated compact electromagnetic sensor as depicted in FIGS. 3A and 3B with two transmitters ($T_1$ and $T_2$) and two receivers ($R_1$ and $R_2$) may be used to measure the permittivity and/or conductivity of a multiphase fluid flowing through a blind-tee conduit. The method for performing such measurements may comprise measuring the signal from a first electromagnetic transmitter to a first electromagnetic receiver separated by a first distance ($r_1$), measuring the signal from the first electromagnetic transmitter to a second electromagnetic receiver separated by a second distance ($r_2$), measuring the signal from a second electromagnetic transmitter to the first electromagnetic receiver separated by a distance substantially equal to the second distance, measuring the signal from the second electromagnetic transmitter to the second electromagnetic receiver separated by a distance substantially equal to the first distance, and wherein the first and second distances are substantially different, followed by combining the four signals to obtain a measurement of the phase-shift and amplitude-attenuation substantially independent of the gain values applied to the receivers and transmitters to provide an estimate of the mixture permittivity and/or conductivity of the multiphase fluid.

Thus, by combining the four signals in a particular manner it is possible to obtain a measure of phase-shift and amplitude-attenuation which is substantially independent of factors other than those provided by the multiphase fluid in the vicinity of the EM sensor(s). Therefore, a more accurate estimate of permittivity and/or conductivity can be obtained and the accuracy is maintained over time, despite drifts which may occur in the gain values of the measurement paths related to both the transmitting and the receiving antennas.

Typically, the transmitting and receiving antennas in the EM sensor are able to operate as a pure magnetic dipole and/or as a pure electric dipole. In some embodiments, they are capable of operating as both pure magnetic and pure electric dipoles.

For example, a simple antenna would be an open-ended coaxial probe that behaves as electric dipoles. A more elaborate design of antenna is shown in EP 1901 094 of the Applicant which is a single-dipole or a cross-dipole of pure magnetic-dipole antennas. Antenna as a superposition of a substantially pure electric dipole and a substantially pure magnetic dipole is shown in EP 1983 357 of the Applicant.

The signals are transmitted and received at one or more frequencies in the radio frequency (RF) and/or microwave frequency spectrum. Merely by way of example, the signals may have a frequency or multiple frequencies of from 300 MHz to 300 GHz.

In some embodiments, at least two transmitters and at least two receivers for each measurement frequency may be used. The four available signals are then combined to eliminate undesirable influencing factors. In such embodiments, the distance between a first transmitter and a first receiver (the first distance) and that between the first transmitter and a second receiver (the second distance) may be significantly different to each other. In some embodiments, the difference of the first and the second distance is at least 10%, more preferably at least 20%.

In some aspects, the distance between a second transmitter and the first receiver is substantially equal to the second distance. Also the distance between a second transmitter to the second receiver may be substantially equal to the first distance. As used herein, the term "substantially equal" means that the distances are within 1% of the first and second distance respectively, preferably within 0.5%.

The transmitters and receivers on an integrated (compact) EM sensor are typically flush-mounted on the inside face of the conduit. The at least two electromagnetic transmitters and at least two electromagnetic receivers are coupled with electromagnetic generation and reception circuitry respectively, and coupled to a microprocessor, wherein the transmitters, receivers, circuitry and the microprocessor are arranged to carry out the method described herein.

The water fraction of the multiphase flow mixture, e.g., the water-in-liquid ratio of the liquid in the vicinity of the EM sensor(s) can be derived from measurements representative of the mixture permittivity and conductivity by the use of appropriate permittivity and conductivity mixing rules. The water conductivity (salinity) can also be determined from the mixture permittivity and conductivity (see U.S. Pat. No. 6,831,470), so that water fraction and WLR estimates can take account of any changes in salinity.

Figure 6:
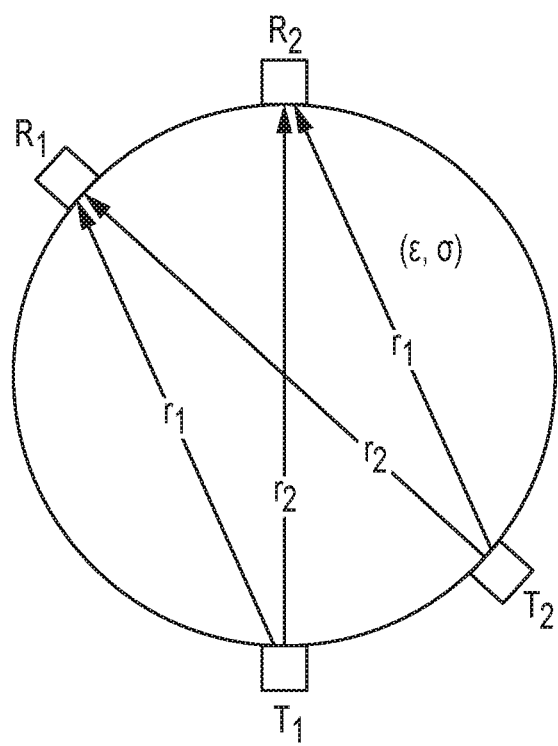
FIG. 6 is a schematic representation of a cross-sectional view through a conduit comprising two transmitters and two receivers arranged to carry out the method of the present invention.

Turning to FIG. 6, four signals can be obtained rapidly from the different T-R combinations of an EM sensor: near and far receiver measurements ($T_1R_1$) and ($T_1R_2$) from the transmitter $T_1$, and near and far receiver measurements ($T_2R_2$) and ($T_2R_1$) from the transmitter $T_2$. These signals depend on the combined antenna element and electronic element gain ($G_T$, $G_R$) of the transmitting and receiving paths (e.g., a function of the transmitter-receiver electric/magnetic dipole areas and their load impedances, gains of transmitting and receiving amplifiers), and on the influence of the multiphase flow medium that may be expressed with a function $\theta$ depending on antennas operating in a pure electric dipole mode or in a pure magnetic dipole mode, or both. This function $\theta$ depends on the wave number k of the flow mixture in the vicinity of the EM sensor and the distance r between the transmitting-receiving antennas, and can be written as (see e.g., EP 1983357 of the Applicant):

$$f(k, r) \propto \begin{cases} \dfrac{e^{ikr}}{2\pi r^3}(1 - ikr) & \text{magnetic-dipole} \\ \dfrac{e^{ikr}}{4\pi r^3}(1 - ikr - k^2 r^2) & \text{electric-diople} \end{cases} \quad (1)$$

Here the wave number k is defined as $$k = \frac{\omega}{c}\sqrt{\varepsilon + i\frac{\sigma}{\omega \varepsilon_o}}, \quad (2)$$

where $\in$ and $\sigma$ are the flow mixture relative permittivity (dielectric constant) and conductivity, respectively; c is the speed of light in vacuum, $\omega$ the angular frequency of transmission RF/microwave, and $\in_0 = 8.854$ pF/m.

With respect to FIG. 6, with a two-transmitter two-receiver configuration (with $r_1$ and $r_2$ being the distances between transmitters and receivers), the following four transmission absolute-measurement signals (being complex of magnitude and phase), rapidly obtainable from each of the four combinations of transmitter and receiving antenna, can be written as:

$$\begin{cases} V_{T_1,R_1} = G_{T_1} G_{R_1} f(k, r_1), & V_{T_1,R_2} = G_{T_1} G_{R_2} f(k, r_2) \\ V_{T_2,R_1} = G_{T_2} G_{R_1} f(k, r_2), & V_{T_2,R_2} = G_{T_2} G_{R_2} f(k, r_1) \end{cases} \quad (3)$$

It can be seen from equation 3 that, the effect of the (short- and long-term) variations in the overall gains ($G_{T1}$, $G_{T2}$, $G_{R1}$, $G_{R2}$) of both the transmitting antennas ($T_1$, $T_2$) and the receiving antennas ($R_1$, $R_2$) influence the signal reading between any one transmitting antenna and any one receiving antenna.

It is possible to rapidly process the ratio of the absolute complex measurement of two of the receivers with respect to a single (common) transmitter ($T_1$ or $T_2$). These signals can be combined and related to the measured attenuation A and phase-shift $\phi$, as follows:

$$A_{T_1} - i\phi_{T_1} \Leftarrow \ln\left(\frac{V_{T_1,R_1}}{V_{T_1,R_2}}\right) = \ln\left(\frac{G_{T_1} G_{R_1} f(k, r_1)}{G_{T_1} G_{R_2} f(k, r_2)}\right) \quad (4a)$$
$$= \ln\left(\frac{G_{R_1} f(k, r_1)}{G_{R_2} f(k, r_2)}\right)$$

$$A_{T_2} - i\phi_{T_2} \Leftarrow \ln\left(\frac{V_{T_2,R_2}}{V_{T_2,R_1}}\right) = \ln\left(\frac{G_{T_2} G_{R_2} f(k, r_1)}{G_{T_2} G_{R_1} f(k, r_2)}\right) \quad (4b)$$
$$= \ln\left(\frac{G_{R_2} f(k, r_1)}{G_{R_1} f(k, r_2)}\right)$$

However, it can be seen from equation 4a or 4b that, the effect of the (short- and long-term) variations in the overall gains ($G_{R1}$, $G_{R2}$) of the receiving antennas ($R_1$, $R_2$) is not removed based on this differential measurement scheme involving combining the signals from one transmitter antenna with two receiving antennas. Note that the antenna spacings ($r_1$, $r_2$) have to be sufficiently different to make possible the determination of the flow mixture wave number k($\in,\sigma$) (of equation 2) from the measured attenuation A and/or phase-shift $\phi$.

However, for scheme comprising the configuration shown in FIG. 6 with two transmitting antennas ($T_1$, $T_2$) and two receiving antennas ($R_1$, $R_2$), and with two known but unequal spacings ($r_1$, $r_2$), the compensation method according to the present invention can then be applied. The compensation method enables eliminating further the effects of the gains of the receiving antennas that may be slightly different. The compensation method effectively involves the averaging of the two differential measurements given in equations 4a and 4b, viz.

$$A_{T_1,T_2} - i\phi_{T_1,T_2} = \frac{(A_{T_1} - i\phi_{T_1}) + (A_{T_2} - i\phi_{T_2})}{2} \Leftarrow \quad (5)$$
$$\frac{1}{2}\left[\ln\left(\frac{G_{R_1} f(k, r_1)}{G_{R_2} f(k, r_2)}\right) + \ln\left(\frac{G_{R_2} f(k, r_1)}{G_{R_1} f(k, r_2)}\right)\right]$$
$$= \ln\left(\frac{f(k, r_1)}{f(k, r_2)}\right)$$

Thus, by rapidly processing the resulting attenuation $A_{T_1,T_2}$ and phase-shift $\phi_{T_1,T_2}$ derived from the signals at the receiving antennas relatively to the two transmitting antennas, operated e.g., according to antennas having pure magnetic dipole mode (see EP 1901094) or having pure electric dipole mode, or having both mode (see EP 1983357), it is possible to determine rapidly the electromagnetic properties (k) of the flow medium by means of a mathematical inversion algorithm.

For example, for the electric and magnetic dipole modes given in equation 1, the theoretical values of the compensated attenuation $A_{T_1,T_2}$ and phase-shift $\phi_{T_1,T_2}$ can be derived as follows:

$$A_{T_1,T_2} - i\phi_{T_1,T_2} \Leftarrow \qquad (6)$$

$$\begin{cases} 3\ln\left(\frac{r_1}{r_2}\right) + ik(r_2 - r_1) + \ln\left(\frac{1 - ikr_1 - k^2r_1^2}{1 - ikr_2 - k^2r_2^2}\right) & \text{electric-dipole} \\ 3\ln\left(\frac{r_1}{r_2}\right) + ik(r_2 - r_1) + \ln\left(\frac{1 - ikr_1}{1 - ikr_2}\right) & \text{magnetic-dipole} \end{cases}$$

Hence, given the transmitter-receiver spacings ($r_1$, $r_2$), from Equation 6, we can have in general the following two set of equations:

$$A_{T_1,T_2} = F_1(k) = F_1(\in, \sigma; \omega)$$

$$\phi_{T_1,T_2} = F_2(k) = F_2(\in, \sigma; \omega) \qquad (7)$$

Based on the compensated attenuation and phase-shift measurements ($A_{T_1,T_2}$, $\phi_{T_1,T_2}$) at one or a plurality of frequencies ($\omega$) that are free from short- and long-term drifts effects of all the sensing antennas and their electronics circuit, the permittivity $\in$ and the conductivity $\sigma$ of a multiphase flow in the sensing region of the EM sensor can be calculated by means of appropriate inversion calculations, from the following set of inverse equations of the Equation 7:

$$\in = F_3(A_{T1,T2}, \phi_{T1,T2}; \omega)$$

$$\sigma = F_4(A_{T1,T2}, \phi_{T1,T2}; \omega) \qquad (8)$$

The early water detection and water volume fraction determination of the flow mixture in the blind-tee can then be derived from the calculated permittivity $\in$ and/or the conductivity $\sigma$ of the flow, by the use of appropriate permittivity and conductivity mixing laws. The water conductivity $\sigma_{water}$ (salinity) can also be determined from the measured the mixture permittivity $\in$ and the mixture conductivity $\sigma$ for a multiphase mixture containing water (see U.S. Pat. No. 6,831,470). This facilitates a water fraction (and WLR) determination in a changing water salinity situation, for example due to formation water breakthrough or water flooding.

Figure 7:
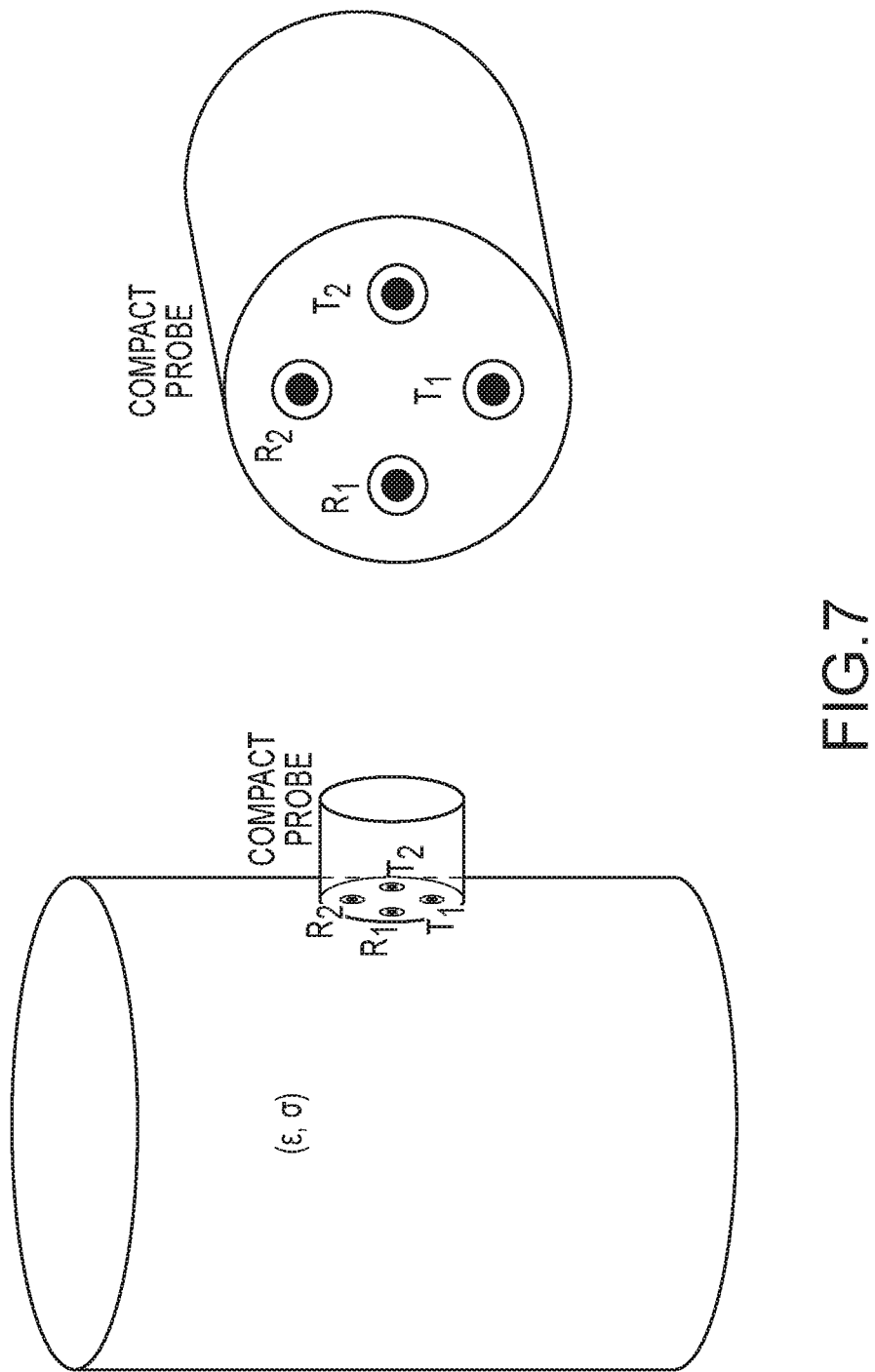
FIG. 7 is a schematic view of a conduit flush mounted with a compact probe (near-wall sensor) comprising two open-ended-coaxial transmitters and two open-ended-coaxial receivers arranged to carry out the method of the present invention.

In some embodiments, as can be seen in FIG. 7 (also in FIG. 3A or FIG. 3B), four signals can be obtained from the different T-R combinations: near and far receiver measurements ($T_1R_1$) and ($T_1R_2$) from the transmitter $T_1$, and near and far receiver measurements ($T_2R_2$) and ($T_2R_1$) from the transmitter $T_2$. It can be appreciated that the measurement region of the compact probe shown in FIG. 7 (or in FIG. 3A, FIG. 3B) is mainly in the vicinity of the 4-antenna aperture, near the pipe conduit inner wall, such as in the liquid-rich regions in blind-tee (FIGS. 1 and 2). These signals depend on the combined antenna element and electronic element gain ($G_T$, $G_R$) of the transmitting and receiving paths (e.g., a function of the transmitter-receiver electric/magnetic dipole areas and their load impedances, gains of transmitting and receiving amplifiers), and on the influence of the multiphase flow medium that may be expressed with a function $\theta$ depending on antennas operating in a pure electric dipole mode or in a pure magnetic dipole mode, or both. This function $\theta$ depends on the wave number k of the flow mixture (equation 2) and the distance r between the transmitting-receiving antennas, and can be written as in equation 1.

With respect to FIG. 7 (FIG. 3A or 3B), with a two-transmitter two-receiver configuration (with $r_1$ and $r_2$ being the distances between transmitters and receivers), four transmission absolute-measurement signals (being complex of magnitude and phase) can be obtained from each of the four combinations of transmitter and receiving antenna, as in equation 3.

Equation 3 shows that the effect of the short- and long-term variations in the overall gains ($G_{T1}$, $G_{T2}$, $G_{R1}$, $G_{R2}$) of both the transmitting antennas ($T_1$, $T_2$) and the receiving antennas ($R_1$, $R_2$) affect the signal reading between any one transmitting antenna and any one receiving antenna.

The ratio of the absolute complex measurement of two of the receivers with respect to a single (common) transmitter ($T_1$ or $T_2$) can be processed to yield the measured attenuation A and phase-shift $\phi$ as in equations 4a and 4b.

Equation 4a or 4b shows that the effect of the short- and long-term variations in the overall gains ($G_{R1}$, $G_{R2}$) of the receiving antennas ($R_1$, $R_2$) is not removed based on the partial differential measurement scheme involving combining the signals from one transmitter antenna with two receiving antennas. The full compensation method enables eliminating further the effects of the gains of the receiving antennas that may be slightly different; it effectively yields the result shown in equation 5 by averaging of the two partial differential measurements given in equations 4a and 4b.

Thus, by processing the resulting attenuation $A_{T_1,T_2}$ and phase-shift $\phi_{T_1,T_2}$ derived from the signals at the receiving antennas relatively to the two transmitting antennas, operated e.g., according to antennas having pure magnetic dipole mode (see EP 1901094) or having pure electric dipole mode, or having both mode (see EP 1983357), the electromagnetic properties (k) of the flow medium (near the aperture of the compact-probe sensor installed in the blind-tee liquid rich regions) may be determined by means of a mathematical inversion algorithm, as in the processing steps shown in equations 6, 7 and 8.

For cross-pipe electromagnetic sensor arrangement shown in FIG. 6, the compensated measurement according to the present invention based on a magnetic dipole mode enables a deep radial depth of investigation into the flow mixture (e.g., into the gas-core in the case of an annular gas-liquid flow). The compensated measurement according to the invention based on an electric dipole mode enables a shallow radial depth of investigation into the flow mixture (e.g., near the liquid annular layer on the pipe wall in the case of an annular gas-liquid flow).

Based on the compensated attenuation and phase-shift measurements ($A_{T_1,T_2}$, $\phi_{T_1,T_2}$) at one or a plurality of frequencies ($\omega$) that are free from short- and long-term drifts effects of all the sensing antennas and their electronics circuit, the permittivity $\in$ and the conductivity $\sigma$ of a multiphase flow (e.g., the entire gas-liquid mixture and/or the liquid annulus in the case of an annular flow) can be calculated by means of appropriate inversion calculations, from the set of inverse equations of the Equation 8.

The water fraction of the flow mixture (e.g., the water-in-liquid-ratio WLR of the liquid annulus in the case of an annular flow) and the gas fraction of the flow mixture (e.g., the gas-core diameter in the case of an annular flow) can then be derived from the calculated permittivity $\in$ and the conductivity $\sigma$ of the flow, by the use of appropriate permittivity and conductivity mixing laws. The water conductivity $\sigma_{water}$ (salinity) can also be determined from the measured the mixture permittivity $\in$ and the mixture conductivity $\sigma$ for a multiphase mixture containing water (see U.S. Pat. No. 6,831,470). This facilitates a water fraction (and WLR) determination in a changing water salinity situation, for example due to formation water breakthrough or water flooding. A robust detection of the water fraction and water-salinity change is also important for subsea-well flow assurance, for the controlled injection of hydrate and/or corrosion inhibitors. Online water-salinity estimate from RF/microwave sensor also enables correction for the mass attenuation coefficients of the water calibration points of a dual-energy or multi-energy nuclear based multiphase flow meter (see U.S. Pat. No. 6,831,470).

Figure 8:
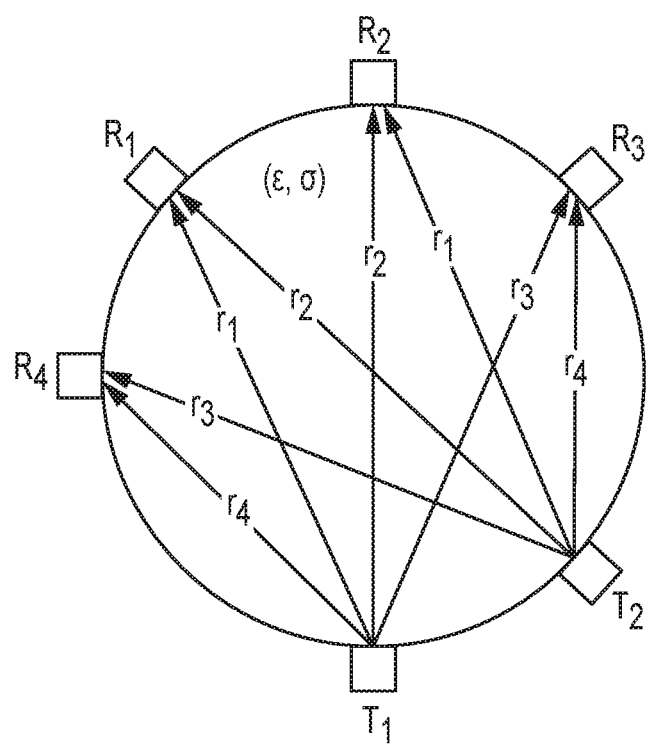
FIG. 8 is a schematic representation of a cross-sectional view through another conduit comprising two transmitters and four receivers arranged to carry out the method of the present invention.

FIG. 8 shows in cross-section, an electromagnetic sensor cross-pipe arrangement of two transmitters, $T_1$ and $T_2$, and four receivers, $R_1$ to $R_4$. It is to be noted that there is a notional line of symmetry passing through the centre of the conduit. In this arrangement the method according to the invention described in relation to FIG. 6 can be carried out in two separate ways. Firstly, the method can be carried out involving transmitters $T_1$ and $T_2$ and receivers $R_1$ and $R_2$. Secondly, it can be carried out involving transmitters $T_1$ and $T_2$ and receivers $R_3$ and $R_4$. This will yield two compensated measurements of phase-shift and amplitude attenuation.

Figure 9:
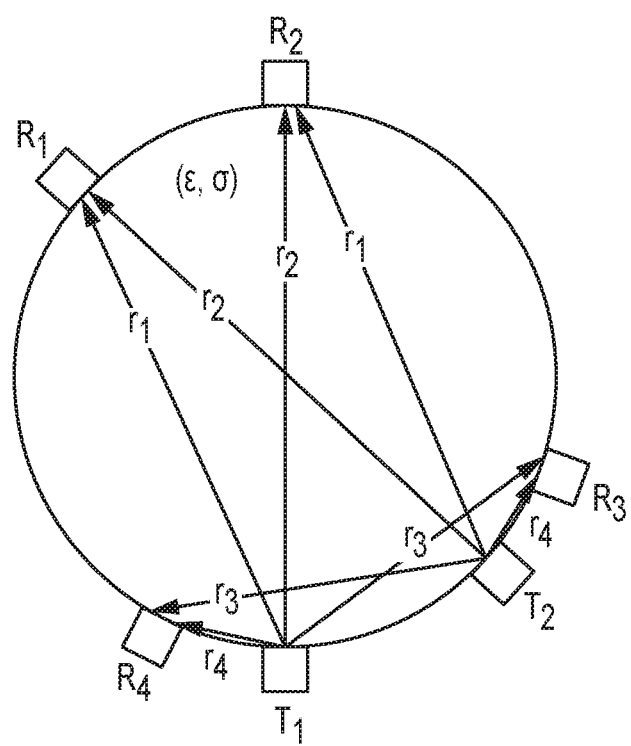
FIG. 9 is a schematic representation of a cross-sectional view of another conduit comprising two transmitters and four receivers arranged to carry out the method of the present invention.

FIG. 9 shows in cross-section, another electromagnetic sensor arrangement of two transmitters $T_1$ and $T_2$ and four receivers $R_1$ to $R_4$. It is again to be noted the notional line of symmetry passing through the centre of the conduit. As for the arrangement shown in FIG. 8, this arrangement can establish two compensated measurements of phase-shift and amplitude attenuation. However, in view of the positioning of $R_3$ and $R_4$, the compensated measurement involving these receivers is sensitive to the fluid properties in the vicinity of the inner wall of the conduit. As the compensated measurement involving $R_1$ and $R_2$ provides flow information cross-pipe, this combination of the compensated measurements can be particularly informative, particularly if there is likely to be an annulus of liquid flowing along the inner wall of the conduit with a gas core in the centre, or if there is a stratified liquid layer at the underside of a horizontal conduit where receivers $R_3$ and $R_4$ (and transmitters $T_1$ and $T_2$) are co-located. Performing compensated measurements at the liquid water-rich region at a pipe underside, such as at the horizontal blind-tee inlet of a multiphase-flowmeter measurement pipe section, provides a more robust detection of water conductivity/salinity at multiphase and/or wet-gas (high gas-volume-fraction) flow conditions. It can be appreciated that a compact probe such as that shown in FIGS. 3A, 3B or FIG. 7 can be used to perform compensated measurement of the properties of liquid (such as WLR, water salinity) in the vicinity of the compact-probe aperture that is preferably installed in a chosen liquid-rich region of a conduit (such as at the horizontal blind-tee inlet of a multiphase-flowmeter measurement pipe section).

Figure 10:
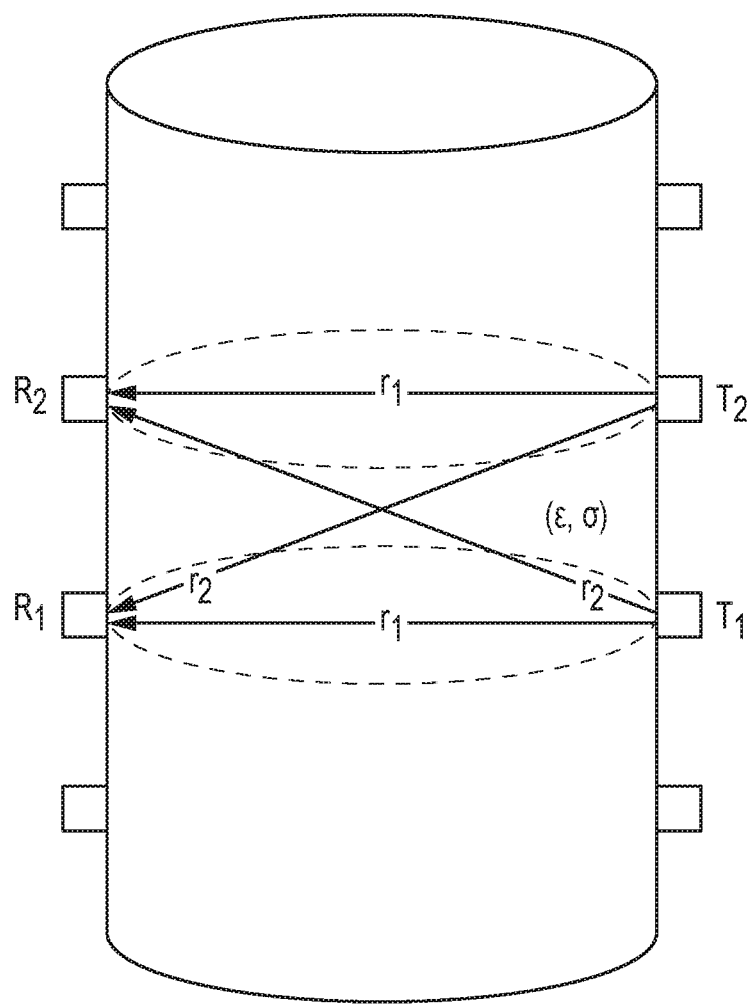
FIG. 10 is a schematic representation in oblique view of another conduit comprising two transmitters and two receivers arranged to carry out the method of the present invention.

FIG. 10 shows, in oblique view, another arrangement of two transmitters $T_1$ and $T_2$ and two receivers $R_1$ and $R_2$. In this arrangement the transmitters and receivers are not all located at the same axial position. However, it is to be noted that there is a line of symmetry passing through the centre of the conduit. The method of the invention as described in relation to the arrangement shown in FIG. 6 can be carried out in the same manner. This arrangement provides information extending along a portion of the length of the conduit, so may provide additional useful information.

Figure 11:
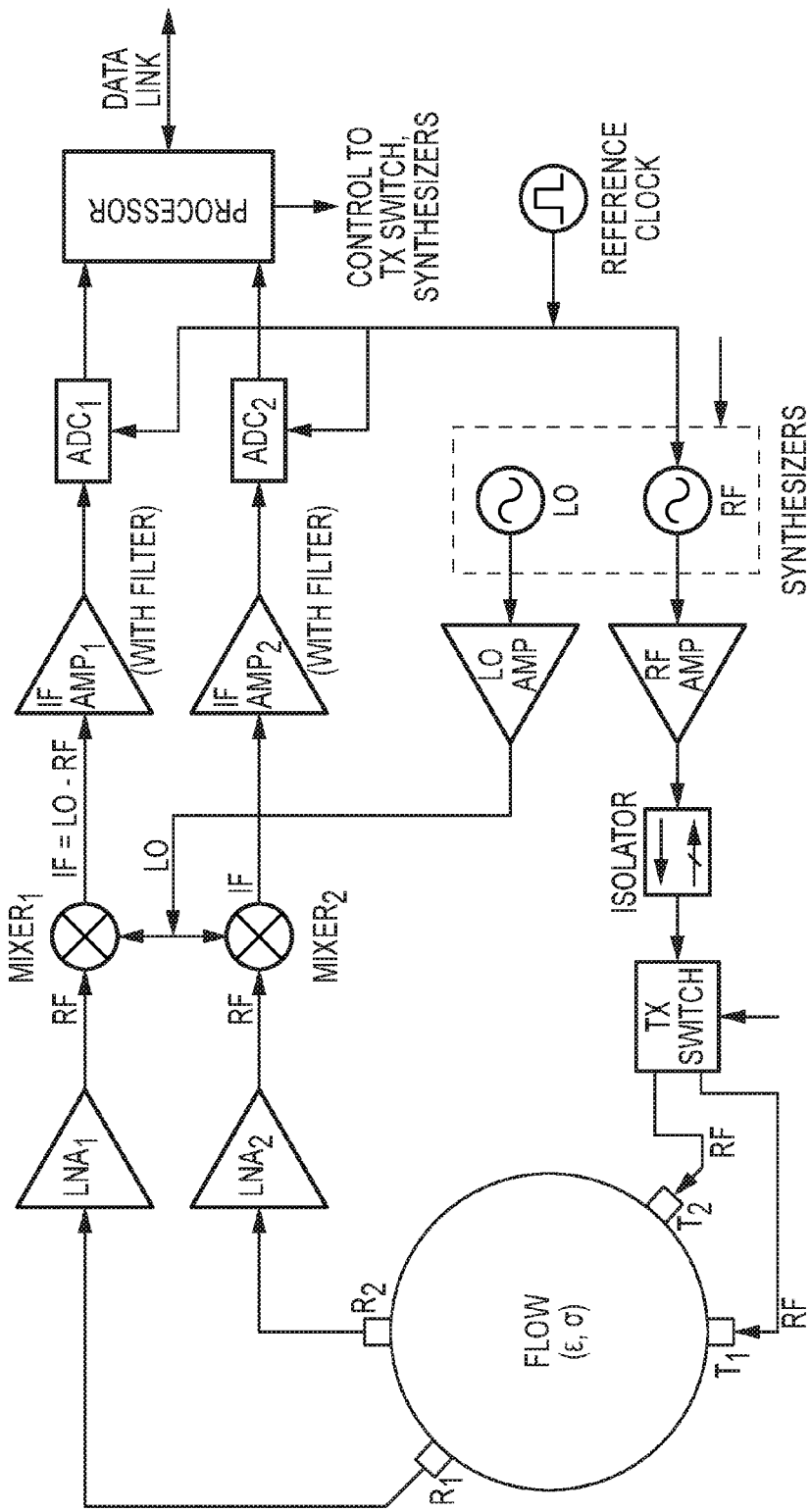
FIG. 11 is a circuit schematic diagram showing how two transmitters and two receivers can be employed according to the method of the invention.

FIG. 11 shows an exemplary schematic circuit diagram for the basic arrangement shown in FIG. 6, or in FIGS. 3A, 3B or FIG. 7 in the case of a compact probe. A radio frequency (RF) synthesizer provides output energy in the microwave or radio frequency region of the spectrum (e.g., from 10 MHz to 10 GHz). A local oscillator frequency (LO) synthesizer is chosen to yield an Intermediate Frequency (IF=LO−RF) which is sufficiently high (e.g., >100 kHz) to enable rapid amplitude-phase measurement of all T-R combinations. The output of the RF synthesizer is coupled through an isolator to an electronic switch (Tx Switch), the two outputs of which connect to the transmitting antennas $T_1$ and $T_2$. The switch is controlled by a control signal from a processor energising each transmitter in turn, e.g., for a few microseconds each.

The receiving antennas $R_1$ and $R_2$ simultaneously detect the RF signal passing through the conduit which pass to a respective low-noise amplifier ($LNA_1$ and $LNA_2$). The amplified RF signals then pass to a respective mixer which is also fed with an appropriately amplified local oscillator (LO) signal. The down-converted $R_1$ and $R_2$ receivers' IF signals are then amplified once more with appropriate low-pass filtering and pass to analogue-to-digital converters for digitization before passing to the processor. The method of the invention can be carried out by suitable comparison of the transmitted and received signals. The amplitude-ratio and phase-difference are calculated by the processor, which also controls the sequencing of the Tx Switch to alternate the two transmitters (and the selection of RF and LO frequencies, amplifiers' gains, etc.). The processor computes compensated transmission attenuation and phase measurements as of equation 5, at a desirable, rapid data rate and/or with proper time averaging, and performs subsequent flow-mixture permittivity and/or conductivity inversions and multiphase-flow phase fraction and/or water conductivity determinations. The processed data can be transmitted through a Data Link for recording/storage/display or further processing with combination of other measurements such as venturi differential-pressure and/or nuclear mixture density.

Figure 12:
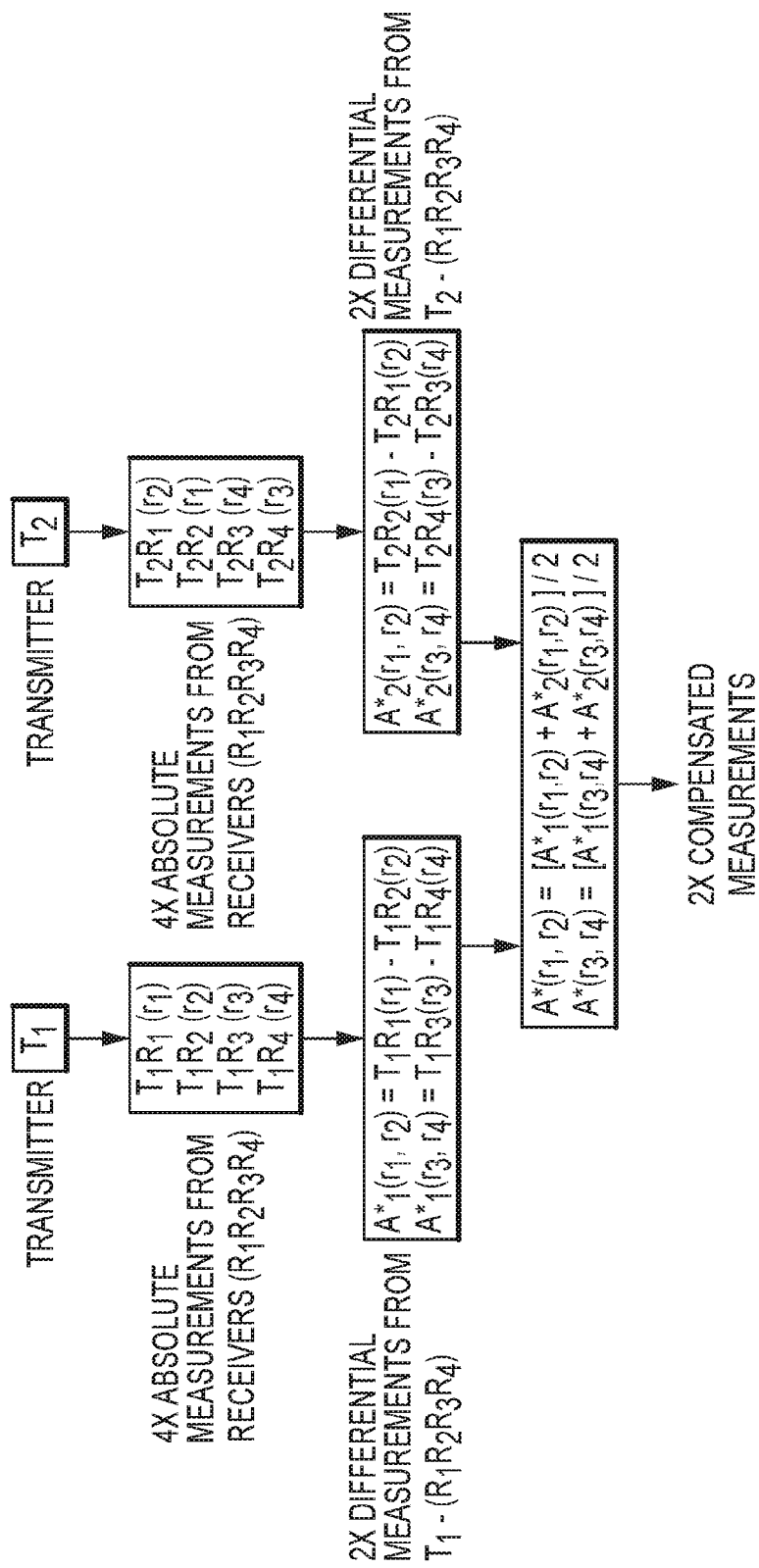
FIG. 12 is a flow chart, illustrating how the signals from an arrangement having two transmitters and four receivers can be combined according to the method of the present invention.

FIG. 12 is a flow diagram, illustrating how the signals from an arrangement comprising two transmitters, $T_1$ and $T_2$, and four receivers, $R_1$ to $R_4$, such as that shown in FIG. 8 or FIG. 9, can be combined to produce two compensated measurements according to the invention.

Figure 13:
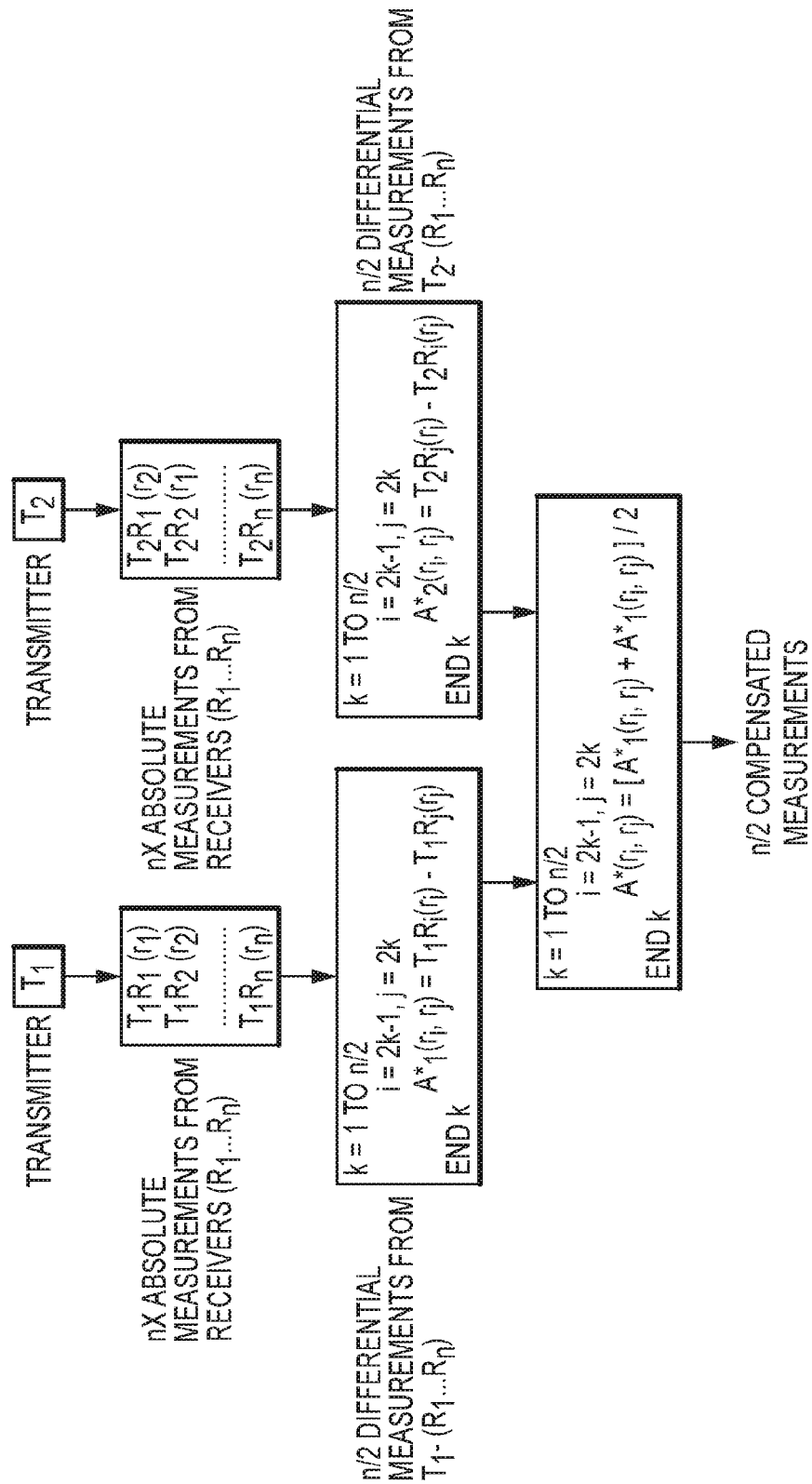
FIG. 13 is a flow chart, illustrating how the signals from a general arrangement having two transmitters and n receivers can be combined according to the method of the present invention.

FIG. 13 is a flow diagram, illustrating how the signals from an arrangement comprising two transmitters, $T_1$ and $T_2$, and n receivers, where n is an even number, can be combined to produce n/2 compensated measurements according to the invention.

The underlying method of compensated measurements of this invention should be applicable to other low-frequency electrical measurement techniques, such as those based on electrical capacitance, electrical resistance or conductance, electrical impedance and/or electrical inductance methods, or based on their combinations. This includes electrical tomography methods involving the use of multiple capacitance, resistance, impedance sensing electrodes, or inductance sensing coils, for performing compensated measurements of various appropriate electrode-pair or coil-pair combinations, in a same pipe cross section or in different pipe cross sections, at vertical, horizontal or other pipe inclinations.

The underlying method of compensated measurements of this invention should be applicable to other higher frequency electrical measurement techniques, such as those based on millimeter-wave (or Terahertz frequency) measurement techniques, including Terahertz tomography-based methods.

Those skilled in the art would appreciate that the underlying method of compensated RF/microwave measurements of this invention for robust mixture permittivity and/or conductivity measurements can be used in combination with a gamma-ray or X-ray densitometer, and in combination with a multi-energy gamma-ray or multi-energy X-ray system.

Further, any of the above can be used in combination with a differential-pressure device. The differential-pressure device is preferably a venturi tube or a venturi nozzle.

While the principles of the disclosure have been described above in connection with specific apparatuses and methods, it is to be clearly understood that this description is made only by way of example and not as limitation on the scope of the invention. Further, the described example embodiments or portions of the described example embodiments may be combined.

What is claimed is:

1. A system for determining water volume fraction, water-in-liquid ratio and/or water conductivity of a multiphase mixture, comprising:
    a blind-tee comprising an inlet, a horizontal conduit, an end section, an outlet and a vertical conduit, wherein:
        the horizontal conduit comprises a first end and a second end and a top section and a bottom section;
        the inlet is disposed at the first end of the horizontal conduit;
        the inlet and the horizontal conduit are configured in use to provide a substantially horizontal flow path for the multiphase mixture flowing into the blind-tee through the inlet and along the horizontal conduit;
        the top section comprises the portion of the horizontal conduit above an imaginary horizontal plane running through the middle of the conduit;
        the bottom section comprises the portion of the horizontal conduit below the imaginary horizontal plane running through the middle of the conduit;
        the vertical conduit joins the horizontal conduit at an opening intermediately between the first end and the second end of the horizontal conduit and the vertical conduit is configured such that it is orthogonal to the imaginary horizontal plane such that in use the multiphase mixture flows through the opening in the horizontal conduit, vertically through the vertical conduit and out of the outlet; and
        the end section is disposed at the second end of the horizontal conduit; and
    at least one electromagnetic sensor coupled with the bottom section and/or the end section of the horizontal conduit where a liquid rich region forms below the imaginary horizontal plane running through the middle of the conduit and configured to measure rapidly at least one value of an amplitude-attenuation, a phase-shift, a conductivity and a permittivity of the multiphase mixture,
        wherein the at least one electromagnetic sensor transmits and/or receives signals at one or more frequencies in the radio frequency and/or microwave frequency spectrum; and
    a processor in communication with the at least one electromagnetic sensor and configured to process at least one of a water volume fraction, a water-in-liquid ratio and a water conductivity of the multiphase mixture from the at least one value of measured amplitude-attenuation, measured phase-shift, measured conductivity and measured permittivity of the multiphase mixture.

2. The system of claim 1, wherein the at least one electromagnetic sensor is coupled with the second end of the horizontal conduit below the imaginary horizontal plane running through the middle of the horizontal conduit.

3. The system of claim 1, wherein the at least one electromagnetic sensor is disposed between the opening at which the vertical conduit joins the horizontal conduit and the second end of the horizontal conduit.

4. The system of claim 3, wherein the at least one electromagnetic sensor is disposed appurtenant to the opening at which the vertical conduit joins the horizontal conduit.

5. The system of claim 1, wherein the vertical conduit extends vertically downwards from the horizontal conduit.

6. The system of claim 5, wherein the at least one electromagnetic sensor is disposed appurtenant to and upstream of the opening at which the vertical conduit joins the horizontal conduit.

7. The system of claim 1, wherein the at least one electromagnetic sensor is disposed substantially flush with an interior wall of the horizontal conduit.

8. The system of claim 1, wherein the at least one electromagnetic sensor comprises at least one electromagnetic transducer operating in the microwave frequency range.

9. The system of claim 1, wherein the at least one electromagnetic sensor comprises at least one of an open-ended coaxial probe antenna and a magnetic dipole antenna.

10. The system of claim 1, wherein the at least one electromagnetic sensor comprises a plug comprising a first electromagnetic transmitter, a second electromagnetic transmitter, a first electromagnetic receiver and a second electromagnetic receiver.

11. The system of claim 10 wherein the first electromagnetic transmitter and the first electromagnetic receiver are separated by a first distance, the first electromagnetic transmitter and the second electromagnetic receiver are separated by a second distance, the first electromagnetic receiver and the second electromagnetic transmitter are separated by a distance substantially equal to the second distance and the second electromagnetic transmitter and the second electromagnetic receiver are separated by a distance substantially equal to the first distance, and wherein the first and second distances are substantially different.

12. The system of claim 1, wherein the at least one electromagnetic sensor comprises at least one magnetic dipole antenna covered by a dielectric window.

13. A method for determining water volume fraction, water-in-liquid ratio and/or water conductivity of a multiphase mixture, comprising:
    flowing the multiphase mixture through a blind-tee comprising an inlet, a horizontal conduit comprising an upper section above a midpoint of the horizontal conduit and a lower section below the midpoint, an end section, a vertical conduit, an opening between the horizontal and the vertical conduits and an outlet, wherein the multiphase mixture is flowed: through the inlet, horizontally through the horizontal conduit, through the opening into the vertical conduit and vertically out of the vertical conduit through the outlet, whereby there is a liquid rich region in the lower section of the horizontal conduit;
    using an electromagnetic system to emit an electromagnetic signal into the multiphase mixture in the horizontal conduit and at least one of measure or receive an output electromagnetic signal, wherein the output electromagnetic signal comprises the emitted electromagnetic signal transmitted through at least a portion of the liquid rich region of the multiphase mixture in the lower section of the horizontal conduit;
    wherein the emitted electromagnetic signal and the output electromagnetic signal are at one or more frequencies in the radio frequency and/or microwave frequency spectrum; and
    processing properties of the multiphase mixture from the output electromagnetic signal to determine water volume fraction, water-in-liquid ratio and/or water conductivity of a multiphase mixture.

14. The method of claim 13, wherein the electromagnetic system is configured to emit the electromagnetic signal into the multiphase mixture at a location which is at least one of a first location in the lower section of the horizontal conduit at the end section, a second location in the lower section of the horizontal conduit between the opening and the end section, a third location in the lower section of the horizontal conduit proximal to the opening, and a fourth location in the lower section of the horizontal conduit below the opening.

15. The method of claim 13, wherein the emitted electromagnetic signal is emitted through a dielectric window.

16. The method of claim 13, wherein the electromagnetic system comprises a transceiver.

17. The method of claim 13, wherein the electromagnetic system comprises at least one electromagnetic transmitter and at least one electromagnetic receiver.

18. The method of claim 13, wherein the electromagnetic system comprises a plug comprising a plurality of electromagnetic transmitters and a plurality of electromagnetic receivers.

19. The method of claim 18, wherein at least one of the plurality of electromagnetic transmitters and the plurality of electromagnetic receivers comprises a transceiver.

20. The method of claim 18, wherein the electromagnetic system is configured to measure a first signal from a first electromagnetic transmitter to a first electromagnetic receiver separated by a first distance, measure a second signal from the first electromagnetic transmitter to a second electromagnetic receiver separated by a second distance, measure a third signal from a second electromagnetic transmitter to the first electromagnetic receiver separated by a distance substantially equal to the second distance, measure a fourth signal from the second electromagnetic transmitter to the second electromagnetic receiver separated by a distance substantially equal to the first distance, and wherein the first and second distances are substantially different.

21. The method of claim 20, further comprising:
processing the first, second, third and fourth signals to obtain at least one of phase-shift and amplitude attenuation independent of gain values applied to the first and second transmitters and receivers; and
processing the at least one of the phase-shift and amplitude attenuation to determine at least one of a permittivity and a conductivity of the multiphase mixture.

22. A system for determining water volume fraction, water-in-liquid ratio and/or water conductivity of a multiphase mixture, comprising:
a blind-tee comprising an inlet, a horizontal conduit, an end section, an outlet and a vertical conduit, wherein:
the horizontal conduit comprises a first end and a second end and a top section and a bottom section;
the inlet is disposed at the first end of the horizontal conduit;
the inlet and the horizontal conduit are configured in use to provide a substantially horizontal flow path for the multiphase mixture flowing into the blind-tee through the inlet and along the horizontal conduit;
the top section comprises the portion of the horizontal conduit above an imaginary horizontal plane running through the middle of the conduit;
the bottom section comprises the portion of the horizontal conduit below the imaginary horizontal plane running through the middle of the conduit;
the end section is disposed at the second end of the horizontal conduit;
the vertical conduit joins the horizontal conduit at an opening intermediately between the first end and the second end of the horizontal conduit and the vertical conduit is configured such that it is orthogonal to the imaginary horizontal plane such that in use the multiphase mixture flows through the opening in the horizontal conduit, vertically through the vertical conduit and out of the outlet; and
two electromagnetic transmitters and two electromagnetic receivers operating at one or more frequencies in the radio frequency and/or microwave frequency spectrum which are coupled with the horizontal conduit at positions such that signals from the transmitters to the receivers pass through the bottom section of the horizontal conduit, the positions being such that the first electromagnetic transmitter and the first electromagnetic receiver are separated by a first distance, the first electromagnetic transmitter and the second electromagnetic receiver are separated by a second distance, the first electromagnetic receiver and the second electromagnetic transmitter are separated by a distance substantially equal to the second distance and the second electromagnetic transmitter and the second electromagnetic receiver are separated by a distance substantially equal to the first distance, and wherein the first and second distances are substantially different; and
a processor in communication with the electromagnetic receivers and configured to process at least one of a water volume fraction, a water-in-liquid ratio and a water conductivity of the multiphase mixture from the electromagnetic signals received by the electromagnetic receivers.

* * * * *